(12) United States Patent
Cardinali et al.

(10) Patent No.: US 12,359,903 B2
(45) Date of Patent: Jul. 15, 2025

(54) SPRING-BASED STATUS SENSORS

(71) Applicant: Insulet Corporation, Acton, MA (US)

(72) Inventors: Steven Cardinali, Tewksbury, MA (US); Kepei Sun, Andover, MA (US); Benjamin Lacroix, Littleton, MA (US)

(73) Assignee: INSULET CORPORATION, Acton, MA (US)

( * ) Notice: Subject to any disclaimer, the term of this patent is extended or adjusted under 35 U.S.C. 154(b) by 384 days.

(21) Appl. No.: 17/826,370

(22) Filed: May 27, 2022

(65) Prior Publication Data

US 2022/0390258 A1    Dec. 8, 2022

Related U.S. Application Data

(60) Provisional application No. 63/194,440, filed on May 28, 2021.

(51) Int. Cl.
| | | |
|---|---|---|
| *G01B 7/00* | (2006.01) | |
| *F04B 51/00* | (2006.01) | |
| *G01D 5/20* | (2006.01) | |

(52) U.S. Cl.
CPC .............. *G01B 7/003* (2013.01); *F04B 51/00* (2013.01); *G01D 5/20* (2013.01)

(58) Field of Classification Search
None
See application file for complete search history.

(56) References Cited

U.S. PATENT DOCUMENTS

| | | |
|---|---|---|
| 441,663 A | 12/1890 | Hofbauer |
| 955,911 A | 4/1910 | Saegmuller |
| 1,441,508 A | 1/1923 | Jensen |
| 2,198,666 A | 4/1940 | Gruskin |
| 2,752,918 A | 7/1956 | Uytenbogaar |
| 3,176,712 A | 4/1965 | Ramsden |
| 3,297,260 A | 1/1967 | Barlow |
| 3,464,359 A | 9/1969 | King |

(Continued)

FOREIGN PATENT DOCUMENTS

| | | |
|---|---|---|
| CA | 606281 A | 10/1960 |
| CA | 2863379 A1 | 8/2013 |

(Continued)

OTHER PUBLICATIONS

European Search Report and Written Opinion for European Patent Application No. EP20174878, dated Sep. 29, 2020, 4 pages.

(Continued)

*Primary Examiner* — Jas A Sanghera

(74) *Attorney, Agent, or Firm* — Goodwin Procter LLP

(57) ABSTRACT

Spring-based sensor devices are described. For example, a spring-based sensor system may include at least one spring associated with a mechanical element, the at least one spring operative to change from a first state to a second state based on a configuration of the mechanical element, sensing circuitry configured to determine an electrical property of the at least one spring, the electrical property to have a first value when the at least one spring is in the first state and a second value when the at least one spring is in the second state, and a logic device to determine a status of the mechanical element based on the electrical property. Other embodiments are described.

19 Claims, 10 Drawing Sheets

(56) References Cited

U.S. PATENT DOCUMENTS

| | | | |
|---|---|---|---|
| 3,825,822 A * | 7/1974 | Forster | G01N 27/9006 |
| | | | 209/570 |
| 3,885,662 A | 5/1975 | Schaefer | |
| 3,946,732 A | 3/1976 | Hurscham | |
| 3,947,692 A | 3/1976 | Payne | |
| 3,993,061 A | 11/1976 | OLeary | |
| 4,108,177 A | 8/1978 | Pistor | |
| 4,152,098 A | 5/1979 | Moody et al. | |
| 4,206,401 A | 6/1980 | Meyer | |
| 4,210,173 A | 7/1980 | Choksi et al. | |
| 4,221,219 A | 9/1980 | Tucker | |
| 4,257,324 A | 3/1981 | Stefansson et al. | |
| 4,268,150 A | 5/1981 | Chen | |
| 4,277,226 A | 7/1981 | Archibald | |
| 4,307,713 A | 12/1981 | Galkin et al. | |
| 4,313,439 A | 2/1982 | Babb et al. | |
| 4,371,790 A | 2/1983 | Manning et al. | |
| 4,398,542 A | 8/1983 | Cunningham et al. | |
| 4,417,889 A | 11/1983 | Choi | |
| 4,424,720 A | 1/1984 | Bucchianeri | |
| 4,435,173 A | 3/1984 | Siposs et al. | |
| 4,475,905 A | 10/1984 | Himmelstrup | |
| 4,498,843 A | 2/1985 | Schneider et al. | |
| 4,507,115 A | 3/1985 | Kambara et al. | |
| 4,551,134 A | 11/1985 | Slavik et al. | |
| 4,560,979 A | 12/1985 | Rosskopf | |
| 4,562,751 A | 1/1986 | Nason et al. | |
| 4,567,549 A | 1/1986 | Lemme | |
| 4,585,439 A | 4/1986 | Michel | |
| 4,587,850 A | 5/1986 | Moser | |
| 4,601,707 A | 7/1986 | Albisser et al. | |
| 4,634,427 A | 1/1987 | Hannula et al. | |
| 4,671,429 A | 6/1987 | Spaanderman et al. | |
| 4,678,408 A | 7/1987 | Nason et al. | |
| 4,684,368 A | 8/1987 | Kenyon | |
| 4,685,903 A | 8/1987 | Cable et al. | |
| 4,755,169 A | 7/1988 | Sarnoff et al. | |
| 4,766,889 A | 8/1988 | Trick et al. | |
| 4,801,957 A | 1/1989 | Vandemoere | |
| 4,808,161 A | 2/1989 | Kamen | |
| 4,836,752 A | 6/1989 | Burkett | |
| 4,846,797 A | 7/1989 | Howson et al. | |
| 4,850,954 A | 7/1989 | Charvin | |
| 4,858,619 A | 8/1989 | Toth | |
| 4,882,600 A | 11/1989 | Van de Moere | |
| 4,898,579 A | 2/1990 | Groshong et al. | |
| 4,908,017 A | 3/1990 | Howson et al. | |
| 4,944,659 A | 7/1990 | Labbe et al. | |
| 4,961,055 A | 10/1990 | Habib et al. | |
| 4,969,874 A | 11/1990 | Michel et al. | |
| 4,973,998 A | 11/1990 | Gates | |
| 4,991,743 A | 2/1991 | Walker | |
| 5,007,458 A | 4/1991 | Marcus et al. | |
| 5,020,325 A | 6/1991 | Henault | |
| 5,045,871 A | 9/1991 | Reinholdson | |
| 5,062,841 A | 11/1991 | Siegel | |
| 5,147,311 A | 9/1992 | Pickhard | |
| 5,178,609 A | 1/1993 | Ishikawa | |
| 5,205,819 A | 4/1993 | Ross et al. | |
| 5,213,483 A | 5/1993 | Flaherty et al. | |
| 5,222,362 A | 6/1993 | Maus et al. | |
| 5,236,416 A | 8/1993 | McDaniel et al. | |
| 5,239,326 A | 8/1993 | Takai | |
| 5,261,882 A | 11/1993 | Sealfon | |
| 5,261,884 A | 11/1993 | Stern et al. | |
| 5,277,338 A | 1/1994 | Divall et al. | |
| 5,281,202 A | 1/1994 | Weber et al. | |
| 5,346,476 A | 9/1994 | Elson | |
| 5,364,342 A | 11/1994 | Beuchat et al. | |
| 5,388,615 A | 2/1995 | Edlund et al. | |
| 5,433,710 A | 7/1995 | VanAntwerp et al. | |
| 5,452,033 A | 9/1995 | Balling et al. | |
| 5,497,804 A * | 3/1996 | Codina | F15B 13/0402 |
| | | | 336/20 |
| 5,503,628 A | 4/1996 | Fetters et al. | |
| 5,520,661 A | 5/1996 | Lal et al. | |
| 5,533,389 A | 7/1996 | Kamen et al. | |
| 5,563,584 A | 10/1996 | Rader et al. | |
| 5,576,781 A | 11/1996 | Deleeuw | |
| 5,582,593 A | 12/1996 | Hultman | |
| 5,585,733 A | 12/1996 | Paglione | |
| 5,586,553 A | 12/1996 | Halili et al. | |
| 5,618,269 A | 4/1997 | Jacobsen et al. | |
| 5,628,309 A | 5/1997 | Brown | |
| 5,637,095 A | 6/1997 | Nason et al. | |
| 5,647,853 A | 7/1997 | Feldmann et al. | |
| 5,660,163 A | 8/1997 | Schulman et al. | |
| 5,665,070 A | 9/1997 | McPhee | |
| 5,713,875 A | 2/1998 | Tanner, II | |
| 5,726,404 A | 3/1998 | Brody | |
| 5,726,751 A | 3/1998 | Altendorf et al. | |
| 5,747,350 A | 5/1998 | Sattler | |
| 5,748,827 A | 5/1998 | Holl et al. | |
| 5,776,103 A | 7/1998 | Kriesel et al. | |
| 5,779,676 A | 7/1998 | Kriesel et al. | |
| 5,785,681 A | 7/1998 | Indravudh et al. | |
| 5,785,688 A | 7/1998 | Joshi et al. | |
| 5,797,881 A | 8/1998 | Gadot | |
| 5,800,397 A | 9/1998 | Wilson et al. | |
| 5,800,420 A | 9/1998 | Gross et al. | |
| 5,807,075 A | 9/1998 | Jacobsen et al. | |
| 5,830,999 A | 11/1998 | Dunn | |
| 5,839,467 A | 11/1998 | Saaski et al. | |
| 5,867,688 A | 2/1999 | Simmon et al. | |
| 5,891,097 A | 4/1999 | Saito et al. | |
| 5,897,530 A | 4/1999 | Jackson | |
| 5,899,882 A | 5/1999 | Waksman et al. | |
| 5,906,597 A | 5/1999 | McPhee | |
| 5,911,716 A | 6/1999 | Rake et al. | |
| 5,919,167 A | 7/1999 | Mulhauser et al. | |
| 5,957,890 A | 9/1999 | Mann et al. | |
| 5,961,492 A | 10/1999 | Kriesel et al. | |
| 5,971,963 A | 10/1999 | Choi | |
| 6,019,747 A | 2/2000 | McPhee | |
| 6,050,457 A | 4/2000 | Arnold et al. | |
| 6,068,615 A | 5/2000 | Brown et al. | |
| 6,159,188 A | 12/2000 | Laibovitz et al. | |
| 6,171,264 B1 | 1/2001 | Bader | |
| 6,174,300 B1 | 1/2001 | Kriesel et al. | |
| 6,190,359 B1 | 2/2001 | Heruth | |
| 6,200,293 B1 | 3/2001 | Kriesel et al. | |
| 6,352,522 B1 | 3/2002 | Kim et al. | |
| 6,363,609 B1 | 4/2002 | Pickren | |
| 6,375,638 B2 | 4/2002 | Nason et al. | |
| 6,381,029 B1 | 4/2002 | Tipirneni | |
| 6,474,219 B2 | 11/2002 | Klitmose et al. | |
| 6,485,461 B1 | 11/2002 | Mason et al. | |
| 6,485,462 B1 | 11/2002 | Kriesel | |
| 6,488,652 B1 | 12/2002 | Weijand et al. | |
| 6,520,936 B1 | 2/2003 | Mann | |
| 6,527,744 B1 | 3/2003 | Kriesel et al. | |
| 6,537,249 B2 | 3/2003 | Kriesell et al. | |
| 6,539,286 B1 | 3/2003 | Jiang | |
| 6,569,115 B1 | 5/2003 | Barker et al. | |
| 6,595,956 B1 | 7/2003 | Gross et al. | |
| 6,656,158 B2 | 12/2003 | Mahoney et al. | |
| 6,685,452 B2 | 2/2004 | Christiansen et al. | |
| 6,699,218 B2 | 3/2004 | Flaherty et al. | |
| 6,723,072 B2 | 4/2004 | Flaherty et al. | |
| 6,740,059 B2 | 5/2004 | Flaherty | |
| 6,749,407 B2 | 6/2004 | Xie et al. | |
| 6,768,319 B2 | 7/2004 | Wang | |
| 6,830,558 B2 | 12/2004 | Flaherty et al. | |
| 6,851,260 B2 | 2/2005 | Mernoe | |
| 6,883,778 B1 | 4/2005 | Newton et al. | |
| 7,018,360 B2 | 3/2006 | Flaherty et al. | |
| 7,104,275 B2 | 9/2006 | Dille | |
| 7,128,727 B2 | 10/2006 | Flaherty et al. | |
| 7,137,964 B2 | 11/2006 | Flaherty | |
| 7,144,384 B2 | 12/2006 | Gorman et al. | |
| 7,160,272 B1 | 1/2007 | Eyal et al. | |
| 7,182,726 B2 | 2/2007 | Williams et al. | |
| 7,303,073 B2 | 12/2007 | Raynal-Olive et al. | |
| 7,303,549 B2 | 12/2007 | Flaherty | |

(56) References Cited

U.S. PATENT DOCUMENTS

| | | |
|---|---|---|
| 7,771,392 B2 | 8/2010 | De Polo et al. |
| 7,914,499 B2 | 3/2011 | Gonnelli et al. |
| 7,951,114 B2 | 5/2011 | Rush et al. |
| 8,056,719 B2 | 11/2011 | Porret et al. |
| 8,105,282 B2 | 1/2012 | Susi et al. |
| 8,267,921 B2 | 9/2012 | Yodfat et al. |
| 8,285,487 B2 | 10/2012 | Bergstrom et al. |
| 8,382,703 B1 | 2/2013 | Abdelaal |
| 8,454,557 B1 | 6/2013 | Qi et al. |
| 8,461,561 B2 | 6/2013 | Freeman et al. |
| 8,499,913 B2 | 8/2013 | Gunter |
| 8,727,117 B2 | 5/2014 | Maasarani |
| 8,905,995 B2 | 12/2014 | Mernoe |
| 8,920,376 B2 | 12/2014 | Caffey et al. |
| 8,939,935 B2 | 1/2015 | OConnor et al. |
| 9,005,166 B2 | 4/2015 | Uber, III et al. |
| 9,180,244 B2 | 11/2015 | Anderson et al. |
| 9,192,716 B2 | 11/2015 | Jugl et al. |
| 9,248,229 B2 | 2/2016 | Devouassoux et al. |
| 9,402,950 B2 | 8/2016 | Dilanni et al. |
| 9,427,710 B2 | 8/2016 | Jansen |
| 9,539,596 B2 | 1/2017 | Ikushima |
| 9,598,195 B2 | 3/2017 | Deutschle et al. |
| 9,862,519 B2 | 1/2018 | Deutschle et al. |
| 10,046,114 B1 | 8/2018 | Biederman et al. |
| 10,086,131 B2 | 10/2018 | Okihara |
| 10,342,926 B2 | 7/2019 | Nazzaro et al. |
| 10,441,717 B2 | 10/2019 | Schmid et al. |
| 10,441,723 B2 | 10/2019 | Nazzaro |
| 10,695,485 B2 | 6/2020 | Nazzaro |
| 2001/0016710 A1 | 8/2001 | Nason et al. |
| 2001/0056258 A1 | 12/2001 | Evans |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0161307 A1 | 10/2002 | Yu et al. |
| 2002/0173769 A1 | 11/2002 | Gray et al. |
| 2002/0173830 A1 | 11/2002 | Starkweather et al. |
| 2003/0019536 A1* | 1/2003 | Smith .................. G08B 21/245 141/18 |
| 2003/0040715 A1 | 2/2003 | DAntonio et al. |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 | 10/2003 | Nason et al. |
| 2003/0199825 A1 | 10/2003 | Flaherty |
| 2004/0010207 A1 | 1/2004 | Flaherty et al. |
| 2004/0010507 A1 | 1/2004 | Bellew |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2004/0085215 A1 | 5/2004 | Moberg et al. |
| 2004/0092865 A1 | 5/2004 | Flaherty et al. |
| 2004/0094733 A1 | 5/2004 | Hower et al. |
| 2004/0153032 A1 | 8/2004 | Garribotto et al. |
| 2004/0215492 A1 | 10/2004 | Choi |
| 2005/0020980 A1 | 1/2005 | Noue et al. |
| 2005/0055242 A1 | 3/2005 | Bello et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe |
| 2005/0277882 A1 | 12/2005 | Kriesel |
| 2006/0041229 A1 | 2/2006 | Garibotto et al. |
| 2006/0060393 A1* | 3/2006 | Fukushima ......... G06F 3/03545 178/20.03 |
| 2006/0079765 A1 | 4/2006 | Neer et al. |
| 2006/0086909 A1 | 4/2006 | Schaber |
| 2006/0092569 A1 | 5/2006 | Che et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0264926 A1 | 11/2006 | Kochamba |
| 2006/0282290 A1 | 12/2006 | Flaherty et al. |
| 2007/0005018 A1 | 1/2007 | Tekbuchava |
| 2007/0027370 A1 | 2/2007 | Brauker et al. |
| 2007/0073236 A1 | 3/2007 | Merno et al. |
| 2007/0078784 A1 | 4/2007 | Donovan et al. |
| 2007/0088271 A1 | 4/2007 | Richards |
| 2007/0118405 A1 | 5/2007 | Campbell et al. |
| 2007/0179885 A1 | 8/2007 | Bird et al. |
| 2007/0191770 A1 | 8/2007 | Moberg et al. |
| 2007/0233051 A1 | 10/2007 | Hohl et al. |
| 2007/0244469 A1 | 10/2007 | Ozeri et al. |
| 2007/0282269 A1 | 12/2007 | Carter et al. |
| 2008/0004515 A1 | 1/2008 | Jennewine |
| 2008/0027371 A1 | 1/2008 | Higuchi et al. |
| 2008/0033272 A1 | 2/2008 | Gough et al. |
| 2008/0051738 A1 | 2/2008 | Griffin |
| 2008/0077081 A1 | 3/2008 | Mounce et al. |
| 2008/0114304 A1 | 5/2008 | Nalesso et al. |
| 2008/0172028 A1 | 7/2008 | Blomquist |
| 2008/0173073 A1 | 7/2008 | Downie et al. |
| 2008/0243211 A1 | 10/2008 | Cartwright et al. |
| 2008/0255438 A1 | 10/2008 | Saidara et al. |
| 2008/0269723 A1 | 10/2008 | Mastrototaro et al. |
| 2008/0281290 A1 | 11/2008 | Yodfat et al. |
| 2008/0294040 A1 | 11/2008 | Mohiuddin et al. |
| 2009/0024083 A1 | 1/2009 | Kriesel et al. |
| 2009/0048556 A1 | 2/2009 | Durand |
| 2009/0062767 A1 | 3/2009 | Van Antwerp et al. |
| 2009/0069787 A1 | 3/2009 | Estes et al. |
| 2009/0112769 A1 | 4/2009 | Dicks et al. |
| 2009/0177142 A1 | 7/2009 | Blomquist et al. |
| 2009/0198215 A1 | 8/2009 | Chong et al. |
| 2009/0254041 A1 | 10/2009 | Krag et al. |
| 2009/0278875 A1 | 11/2009 | Holm et al. |
| 2009/0326472 A1 | 12/2009 | Carter et al. |
| 2010/0036326 A1 | 2/2010 | Matusch |
| 2010/0076275 A1 | 3/2010 | Chu et al. |
| 2010/0094251 A1 | 4/2010 | Estes |
| 2010/0114026 A1 | 5/2010 | Karratt et al. |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0185175 A1 | 7/2010 | Kamen et al. |
| 2010/0241066 A1 | 9/2010 | Hansen et al. |
| 2010/0286997 A1 | 11/2010 | Srinivasan |
| 2011/0054399 A1 | 3/2011 | Chong et al. |
| 2011/0073620 A1 | 3/2011 | Verrilli |
| 2011/0124996 A1 | 5/2011 | Reinke et al. |
| 2011/0142688 A1 | 6/2011 | Chappel et al. |
| 2011/0144586 A1 | 6/2011 | Michaud et al. |
| 2011/0152658 A1 | 6/2011 | Peyser et al. |
| 2011/0180480 A1 | 7/2011 | Kloeffel et al. |
| 2011/0213306 A1 | 9/2011 | Hanson et al. |
| 2011/0218495 A1 | 9/2011 | Remebe |
| 2011/0225024 A1 | 9/2011 | Seyer et al. |
| 2011/0230833 A1 | 9/2011 | Landman et al. |
| 2011/0246235 A1 | 10/2011 | Powell et al. |
| 2011/0313680 A1 | 12/2011 | Doyle, III |
| 2011/0316562 A1 | 12/2011 | Cefai et al. |
| 2012/0029941 A1 | 2/2012 | Malave et al. |
| 2012/0050046 A1 | 3/2012 | Satorius et al. |
| 2012/0054841 A1 | 3/2012 | Schultz et al. |
| 2012/0078161 A1 | 3/2012 | Masterson et al. |
| 2012/0153936 A1 | 6/2012 | Romani et al. |
| 2012/0203085 A1 | 6/2012 | Tsukamoto |
| 2012/0172817 A1 | 7/2012 | Bruggemann et al. |
| 2012/0182939 A1 | 7/2012 | Rajan et al. |
| 2012/0184909 A1 | 7/2012 | Gyrn |
| 2012/0209207 A1 | 8/2012 | Gray et al. |
| 2012/0232520 A1 | 9/2012 | Sloan et al. |
| 2012/0265166 A1 | 10/2012 | Yodfat |
| 2012/0277667 A1 | 11/2012 | Yodat et al. |
| 2013/0006213 A1 | 1/2013 | Arnitz et al. |
| 2013/0017099 A1 | 1/2013 | Genoud |
| 2013/0030841 A1 | 1/2013 | Bergstrom et al. |
| 2013/0036100 A1 | 2/2013 | Nagpal et al. |
| 2013/0060194 A1 | 3/2013 | Rostein |
| 2013/0064701 A1 | 3/2013 | Konishi |

(56) References Cited

U.S. PATENT DOCUMENTS

| | | |
|---|---|---|
| 2013/0080832 A1 | 3/2013 | Dean et al. |
| 2013/0138452 A1 | 5/2013 | Cork et al. |
| 2013/0173473 A1 | 7/2013 | Birtwhistle et al. |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0274576 A1 | 10/2013 | Amirouche et al. |
| 2013/0296792 A1 | 11/2013 | Cabiri |
| 2014/0018730 A1 | 1/2014 | Muller-Pathle |
| 2014/0052055 A1 | 2/2014 | Yodfat et al. |
| 2014/0114277 A1 | 4/2014 | Eggert et al. |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0163664 A1 | 6/2014 | Goldsmith |
| 2014/0171901 A1 | 6/2014 | Langsdorf et al. |
| 2014/0180203 A1 | 6/2014 | Budiman et al. |
| 2015/0038898 A1 | 2/2015 | Palmer et al. |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0057913 A1 | 2/2015 | Benhammou |
| 2015/0064036 A1 | 3/2015 | Eberhard |
| 2015/0119666 A1 | 4/2015 | Brister et al. |
| 2015/0137017 A1 | 5/2015 | Ambrosina et al. |
| 2015/0202386 A1 | 7/2015 | Brady et al. |
| 2015/0290389 A1 | 10/2015 | Nessel |
| 2015/0290391 A1 | 10/2015 | Schmid et al. |
| 2015/0297825 A1 | 10/2015 | Focht et al. |
| 2016/0008549 A1 | 1/2016 | Plumptre et al. |
| 2016/0015957 A1* | 1/2016 | Tieck .................. A61M 5/1456 604/533 |
| 2016/0022905 A1 | 1/2016 | Nagar et al. |
| 2016/0025544 A1 | 1/2016 | Kamer |
| 2016/0055842 A1 | 2/2016 | Defranks et al. |
| 2016/0082242 A1 | 3/2016 | Burton et al. |
| 2016/0129190 A1 | 5/2016 | Haitsuka |
| 2016/0184517 A1 | 6/2016 | Baek et al. |
| 2016/0193423 A1 | 7/2016 | Bilton |
| 2016/0213851 A1 | 7/2016 | Weibel et al. |
| 2016/0339172 A1 | 11/2016 | Michaud et al. |
| 2017/0021096 A1 | 1/2017 | Cole et al. |
| 2017/0021137 A1 | 1/2017 | Cole |
| 2017/0089730 A1* | 3/2017 | Utermoehlen ......... G01D 5/243 |
| 2017/0100541 A1 | 4/2017 | Constantineau et al. |
| 2017/0173261 A1 | 6/2017 | O'Connor et al. |
| 2017/0216516 A1 | 8/2017 | Dale |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0040255 A1 | 2/2018 | Freeman et al. |
| 2018/0185579 A1 | 7/2018 | Joseph et al. |
| 2018/0280609 A1 | 10/2018 | Nishimura et al. |
| 2018/0296757 A1 | 10/2018 | Finan et al. |
| 2018/0310954 A1* | 11/2018 | Almoumen ............. A61M 5/24 |
| 2018/0313346 A1 | 11/2018 | Oakes |
| 2019/0192782 A1 | 6/2019 | Pedersen et al. |
| 2019/0365993 A1 | 12/2019 | Staub et al. |
| 2020/0009315 A1 | 1/2020 | Brouet et al. |
| 2020/0188586 A1 | 6/2020 | Sims et al. |
| 2020/0345931 A1 | 11/2020 | Gray et al. |

FOREIGN PATENT DOCUMENTS

| | | |
|---|---|---|
| CN | 1375338 A | 10/2002 |
| CN | 201134101 Y | 10/2008 |
| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 4200595 A1 | 7/1993 |
| DE | 19723648 C1 | 8/1998 |
| DE | 102005040344 A1 | 3/2007 |
| EP | 0454331 A1 | 10/1991 |
| EP | 0789146 A1 | 8/1997 |
| EP | 867196 A2 | 9/1998 |
| EP | 1065378 A2 | 1/2001 |
| EP | 1177802 A1 | 2/2002 |
| EP | 1403519 A1 | 3/2004 |
| EP | 1762263 A1 | 3/2007 |
| EP | 1839694 A1 | 10/2007 |
| EP | 1852703 A1 | 11/2007 |
| EP | 2099384 A1 | 9/2009 |
| EP | 2353628 A2 | 8/2011 |
| EP | 2397181 A1 | 12/2011 |
| EP | 2468338 A1 | 6/2012 |
| EP | 2703024 A1 | 3/2014 |
| EP | 1874390 B1 | 10/2014 |
| EP | 2830499 A1 | 2/2015 |
| EP | 3068290 A1 | 9/2016 |
| EP | 3187201 A1 | 7/2017 |
| EP | 3598942 A1 | 1/2020 |
| EP | 3607985 A1 | 2/2020 |
| ES | 2559866 T3 | 2/2016 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 1401588 A | 7/1975 |
| GB | 2008806 A | 6/1979 |
| GB | 2077367 A | 12/1981 |
| GB | 2176595 A | 12/1986 |
| GB | 2443260 A | 4/2008 |
| GB | 2443261 A | 4/2008 |
| GB | 2456681 A | 7/2009 |
| GB | 2461086 A | 12/2009 |
| GB | 2495014 A | 3/2013 |
| GB | 2524717 A | 10/2015 |
| GB | 2525149 A | 10/2015 |
| GB | 2549750 A | 11/2017 |
| IL | 46017 A | 11/1977 |
| JP | 06063133 A | 3/1994 |
| JP | 106296690 A | 10/1994 |
| JP | H08238324 A | 9/1996 |
| JP | 2001190659 A | 7/2001 |
| JP | 2003154190 A | 5/2003 |
| JP | 2004247271 A | 9/2004 |
| JP | 2004274719 A | 9/2004 |
| JP | 2005188355 A | 7/2005 |
| JP | 2006159228 A | 6/2006 |
| JP | 6098988 B2 | 9/2006 |
| JP | 2006249130 A | 9/2006 |
| JP | 2007144141 A1 | 6/2007 |
| JP | 2007307359 A | 11/2007 |
| JP | 2008242502 A | 10/2008 |
| JP | 2009514580 A | 4/2009 |
| JP | 2012210441 A | 11/2012 |
| JP | 2017513577 A | 6/2017 |
| NL | 1019126 C1 | 4/2003 |
| WO | 8101658 A1 | 6/1981 |
| WO | 8606796 A1 | 11/1986 |
| WO | 9320864 A1 | 10/1993 |
| WO | 9415660 A1 | 7/1994 |
| WO | 9801071 A1 | 1/1998 |
| WO | 9819145 A1 | 5/1998 |
| WO | 9824495 A1 | 6/1998 |
| WO | 9841267 A1 | 9/1998 |
| WO | 9855073 A1 | 12/1998 |
| WO | 9856293 A1 | 12/1998 |
| WO | 9910040 A1 | 3/1999 |
| WO | 9910049 A1 | 3/1999 |
| WO | 9962576 A1 | 12/1999 |
| WO | 0010628 A2 | 3/2000 |
| WO | 0013580 A1 | 3/2000 |
| WO | 0019887 A1 | 4/2000 |

(56) References Cited

FOREIGN PATENT DOCUMENTS

| | | |
|---|---|---|
| WO | 0029047 A1 | 5/2000 |
| WO | 0061215 A1 | 10/2000 |
| WO | 0078210 A1 | 12/2000 |
| WO | 0178812 A1 | 10/2001 |
| WO | 0220073 A2 | 3/2002 |
| WO | 0226282 A2 | 4/2002 |
| WO | 2002076535 A1 | 4/2002 |
| WO | 2003097133 A1 | 4/2002 |
| WO | 02068823 A1 | 9/2002 |
| WO | 2004032994 A2 | 4/2004 |
| WO | 2004056412 A2 | 7/2004 |
| WO | 2004110526 A1 | 12/2004 |
| WO | 2005031631 A2 | 4/2005 |
| WO | 2006060668 A2 | 6/2006 |
| WO | 2007066152 A2 | 6/2007 |
| WO | 2007112034 A2 | 10/2007 |
| WO | 2008024814 A2 | 2/2008 |
| WO | 2008133702 A1 | 11/2008 |
| WO | 2009023634 A2 | 2/2009 |
| WO | 2009032399 A1 | 3/2009 |
| WO | 2009039203 A2 | 3/2009 |
| WO | 2009141005 A1 | 11/2009 |
| WO | 2010022069 A2 | 2/2010 |
| WO | 2010025433 A1 | 3/2010 |
| WO | 2010077279 A1 | 7/2010 |
| WO | 2010078434 A2 | 7/2010 |
| WO | 2010139793 A1 | 12/2010 |
| WO | 2010146579 A1 | 12/2010 |
| WO | 2011010198 A2 | 1/2011 |
| WO | 2011012465 A1 | 2/2011 |
| WO | 2011031458 A1 | 3/2011 |
| WO | 2011069935 A2 | 6/2011 |
| WO | 2011075042 A1 | 6/2011 |
| WO | 2011133823 A1 | 10/2011 |
| WO | 2012073032 A1 | 6/2012 |
| WO | 2013050535 A2 | 4/2013 |
| WO | 2013137893 A1 | 9/2013 |
| WO | 2013149186 A1 | 10/2013 |
| WO | 2014029416 A1 | 2/2014 |
| WO | 2014136105 A1 | 9/2014 |
| WO | 2014149357 A1 | 9/2014 |
| WO | 2014179774 A1 | 11/2014 |
| WO | 2015032772 A1 | 3/2015 |
| WO | 2015048791 A1 | 4/2015 |
| WO | 2015081337 A2 | 6/2015 |
| WO | 2015117854 A1 | 8/2015 |
| WO | 2015167201 A1 | 11/2015 |
| WO | 2015177082 A1 | 11/2015 |
| WO | 2015187793 A1 | 12/2015 |
| WO | 2016041873 A1 | 3/2016 |
| WO | 2016181384 A2 | 11/2016 |
| WO | 2016209554 A1 | 12/2016 |
| WO | 2017089289 A1 | 6/2017 |
| WO | 2017148855 A1 | 9/2017 |
| WO | 2017187177 A1 | 11/2017 |
| WO | 2017205816 A1 | 11/2017 |
| WO | 2019043702 A1 | 3/2019 |
| WO | 2019094440 A1 | 5/2019 |
| WO | 2020124058 A1 | 6/2020 |
| WO | 2021016452 A1 | 1/2021 |

OTHER PUBLICATIONS

Schott web-page image from Jul. 9, 2016, https://www.us.schott.com/pharmaceutical_packaging/english/products/cartridges.html.
International Search Report and Written Opinion for International Patent Application No. PCT/US2021/055581, dated Feb. 8, 2022, 19 pages.
International Search Report and Written Opinion for International Patent Application No. PCT/US2022/011356, dated Apr. 29, 2022, 19 pages.
International Search Report and Written Opinion for International Patent Application No. PCT/US2022/031354, mailed Aug. 17, 2022, 12 pages.
International Search Report and Written Opinion for PCT/US2018/014351, mailed on Jun. 4, 2018, 9 pages.
Lind et al. "Linear Motion Miniature Actuators." Paper presented at the 2nd Tampere International Conference on Machine Automation, Tampere, Finland (Sep. 1998).
Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.
Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.
Vaughan, M.E., "The Design, Fabrication, and Modeling of a Piezoelectric Linear Motor." Master's thesis, Virginia Polytechnic Institute and State University, VA. (2001).
Galante et al., "Design, Modeling, and Performance of a High Force Piezoelectric Inchworm Motor," Journal of Intelligent Material Systems and Structures, vol. 10, 962-972 (1999).
International Search Report and Written Opinion for International Application No. PCT/US2017/055054, mailed on Jan. 25, 2018, 13 pages.
International Search Report and Written Opinion for International Application No. PCT/US2018/045155, mailed on Oct. 15, 2018, 15 pages.
International Preliminary Report on Patentability for International Application No. PCT/US2017/034811 issued on Nov. 27, 2018, 10 pages.
International Preliminary Report on Patentability for International Patent Application No. PCT/US2017/046508, Feb. 12, 2019, 10 pages.
International Search Report and Written Opinion for International Application No. PCT/US2017/046508, mailed on Jan. 17, 2018, 14 pages.
International Search Report and Written Opinion for International Application No. PCT/US2017/046777, mailed on Dec. 13, 2017, 14 pages.
International Search Report and Written Opinion for International Application No. PCT/US2017/046737, mailed on Dec. 14, 2017, 11 pages.
International Search Report and Written Opinion for International Application No. PCT/US2017/034814, mailed on Oct. 11, 2017, 18 pages.
European Search Report and Written Opinion for the European Patent Application No. EP19177571, dated Oct. 30, 2019, 8 pages.
International Preliminary Report on Patentability for International Patent Application No. PCT/US2018/014351, dated Jul. 23, 2019, 7 pages.
International Preliminary Report on Patentability for International Patent Application No. PCT/US2017/046777, dated Feb. 19, 2019, 8 pages.
International Preliminary Report on Patentability for International Patent Application No. PCT/US2017/046737, dated Feb. 19, 2019, 8 pages.
International Preliminary Report on Patentability for International Patent Application No. PCT/US2017/055054, dated Apr. 9, 2019, 8 pages.
International Search Report and Written Opinion for Application No. PCT/US2017/034811, mailed Oct. 18, 2017, 15 pages.
EPO Search Report received in Application No. 13768938.6, dated Nov. 11, 2015, 8 pages.
International Search Report and Written Opinion for PCT Application No. PCT/US13/34674, mailed Aug. 6, 2013, 17 pages.
International Search Report and Written Opinion for International Application No. PCT/GB2007/004073, Jan. 31, 2008, 8 pages.
International Search Report and Written Opinion for International Patent Application No. PCT/US2019/063615, dated May 3, 2020, 17 pages.
International Preliminary Report on Patentability for International Patent Application No. PCT/US2018/045155, dated Feb. 14, 2020, 10 pages.

(56) References Cited

OTHER PUBLICATIONS

International Search Report and Written Opinion for International Patent Application No. PCT/US2019/035756, dated Jul. 31, 2019, 11 pages.
European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
U.K. Intellectual Property Office, GB Application No. GB 1401587.9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.
U.K. Intellectual Property Office, GB Application No. GB 1401588.7, "Search Report under Section 17(5)" Aug. 17, 2015, 1 page.
U.K. Intellectual Property Office, GB Application No. GB 1401589.5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 pages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
International Search Report and Written Opinion for International Patent Application No. PCT/US2022/029012, mailed Aug. 19, 2022, 12 pages.
International Search Report and Written Opinion for PCT Application No. PCT/US2019/059854, mailed Aug. 26, 2020, 15 pages.
International Search Report and Written Opinion, Application No. PCT/US2022/016713, mailed Aug. 5, 2022, 19 pages.
International Search Report and Written Opinion for the International Patent Application No. PCT/US2021/047690, mailed Jan. 14, 2022, 13 pages.
International Search Report and Written Opinion for the International Patent Application No. PCT/US2022/055745, mailed Feb. 14, 2022, 13 pages.
International Search Report and Written Opinion for the International Patent Application No. PCT/US2021/053162, mailed Mar. 28, 2022, 18 pages.
International Search Report and Written Opinion for the International Patent Application No. PCT/US2021/064041, mailed Apr. 29, 2022, 11 pages.
International Search Report and Written Opinion for the International Patent Application No. PCT/US2022/015809, mailed Jun. 20, 2022, 15 pages.

\* cited by examiner

SPRING-BASED STATUS SENSORS

RELATED APPLICATIONS

This application claims the benefit of U.S. Provisional Patent Application No. 63/194,440, filed May 28, 2021, the contents of which are incorporated herein by reference in their entirety.

FIELD OF THE INVENTION

The present disclosure generally relates to spring-based status sensors, for example, for determining a status of a mechanical device associated with a spring element based on at least one electrical property, such as the inductance, of the spring element.

BACKGROUND

Mechanical actuation systems may operate using resilient elements, such as a spring or spring-based component. The electrical properties of springs may be used to determine information about the spring such as the length (for instance, the amount of extension/compression). For example, the inductance of a spring varies in inverse proportion to its length. However, the practical application of the electrical properties of a spring in real-world devices, outside of laboratory conditions, is challenging using conventional techniques. For instance, in real-world devices, conventional measurement methods are generally unreliable and error-prone because the inductance detection is subject to interference and noise from various sources.

The lack of reliable methods for determining the status of spring-based elements is particularly acute in small-scale devices, such as a fluid pump in a wearable medicament delivery device. Determining operational information for a wearable medicament delivery device and individual components is key to maintaining proper functioning and ensuring patient safety during use. However, smaller component sizes and footprint constraints make it more challenging to sense component status information. For example, spring elements used in wearable medicament delivery device fluid pump devices are much smaller than those used in typical pump systems. As a result, the detectable inductance ranges for fluid pump spring elements in conventional wearable medicament delivery devices are too low to provide meaningful status information. Furthermore, limited space precludes the addition of conventional amplifiers or other elements that may boost electrical signals, such as inductance. As a result, conventional devices are not able to determine spring element information accurately and reliably, particularly for devices in small form factors, such as a wearable medicament delivery device.

Figure 1:
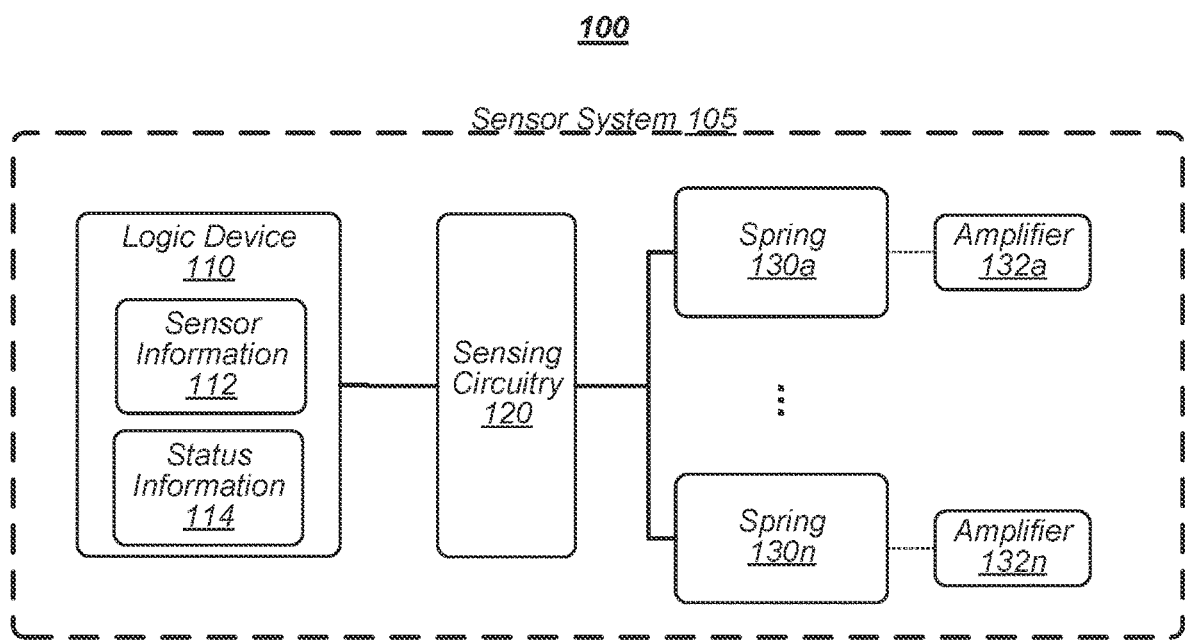
FIG. 1 illustrates a first exemplary embodiment of an operating environment in accordance with the present disclosure.

The drawings are not necessarily to scale. The drawings are merely representations, not intended to portray specific parameters of the disclosure. The drawings are intended to depict example embodiments of the disclosure, and therefore should not be considered as limiting in scope. In the drawings, like numbering represents like elements.

DETAILED DESCRIPTION

The described technology generally relates to spring- or coil-based status sensors for determining an operational status or other information of a mechanical (or semi-mechanical) device. In some embodiments, a sensor system may include a spring or spring-based element operably coupled to sensing circuitry. A non-limiting example of a spring may include a compression spring (see, for example, FIGS. 5A and 5B). The spring may be electrically active, for instance, arranged as a part of the sensing circuitry. The sensing circuitry may operate to receive, detect, determine, measure, translate, or otherwise process electrical information from the spring. The electrical information may include and/or may be used to determine spring status information, indicating a status of the spring. A non-limiting example of electrical information may include the inductance of the spring. The inductance may indicate a length of the spring (for instance, an amount of compression), which, in turn, may be used to determine an operational characteristic of a mechanical device associated with the spring. For example, the length of the spring may be associated with the position or other status of a piston of a fluid pump system. A determination of the length of the spring may be used to determine a position of the piston and, therefore, a status of the pump (for instance, a spring length greater than X may indicate that the piston is in a status of drawing in fluid into a pump chamber from a reservoir, a spring length less than X may indicate that the piston is in a status of ejecting fluid through a fluid path, and/or the like).

Springs are often used in a wide range of mechanical actuation systems. Conventionally, the spring status can be detected by various methods including string gauge or inductance measurements. String gauge requires delicate amplification and analog to digital conversion, which add complexity in electronic system implementation, and, therefore, are not a feasible solution, particularly for low-cost embedded systems.

The measurement of electrical characteristics, such as the inductance, of a spring may assist in identifying the status of the spring. However, the sensing of the electrical characteristics of a spring, particularly arranged among multiple other components, are subject to interference, noise, and other effects that degrade any detectable signal of the spring electrical characteristics. The ability to use springs as sensing elements is particularly challenging using conventional technology in small form factors, where springs may be on the millimeter (mm) scale (for instance, about 2 mm to about 5 mm). Within such a small scale environment, the inductance of a spring may only be about 60 nanohenrys (nH) to about 90 nH. This inductance range may be too small to be reliably detected by current devices (or without requiring intensive computations), particularly that are able to fit within a user product, such as a wearable fluid delivery device. Accordingly, some embodiments may use an amplifier device to amplify the electrical characteristics of a spring. In some embodiments, for example, an amplifier device may be used to boost the intrinsic inductance value of a spring to increase the inductance range of detection. In some embodiments, the amplifier device may be or may include a magnetic material that is arranged within the internal (empty) space of the spring. In various embodiments, the magnetic material may be in the form of a cylinder arranged in the internal space of the spring, which, for example, may operate the same or similar to a solenoid from a magnetostatics perspective. In some embodiments, the axis of the magnetic cylinder may be aligned with the axis of the spring or solenoid to increase the inductance range of the solenoid. In some embodiments, the amplifier device may be used within a low-cost system based on a low-power microcontroller unit with limited performance characteristics. In this manner, the electrical characteristics of a spring of a spring-based sensor device may be amplified without requiring additional space or complex and/or expensive components.

In some embodiments, the spring-based status sensors may use sensing circuitry that includes an electronic oscillator. In various embodiments, the electronic oscillator may be or may include an inductor-capacitor (LC) oscillator. In exemplary embodiments, the electronic oscillator may be or may include a Colpitts oscillator. In various embodiments, the detection of the status of the spring may be determined via the measurement of the spring-coil's inductance. The inductance measurement may be translated from the oscillation frequencies of the single Colpitts oscillator and cross-coupled oscillators for single-spring system and two-spring system, respectively. The sensing circuitry may not need sinusoidal wave synthesizer, precision analog-to-digital convertor, phase loop lock, and/or other complicated analog circuit. Rather, for example, simple, low-cost components such as microcontroller (MCU) with a generic counter/timer module for robust inductance measurement, which reduces system cost, complexity, and required footprint may be used according to some embodiments.

In various embodiments, the spring-based status sensors may be used within a wearable fluid delivery device for delivering a fluid to a patient. In some embodiments, the fluid may be or may include a medicament. The wearable fluid delivery device may include a reservoir for holding the fluid, a fluid path in fluid communication with the reservoir, a needle in fluid communication with the fluid path to deliver the fluid to the patient wearing the wearable fluid delivery device, and a fluid delivery pump configured to force the fluid from the reservoir, through the fluid delivery path, and into the patient via the needle. In some embodiments, a spring-based status sensor may be configured to determine a step, process, sequence, or other operational information of the fluid delivery pump For example, the spring-based status sensor may be able to determine a length of a spring based on a measured inductance of the spring. In one example, a spring may have a compressed length of about 2 mm and an extended (for instance, non-compressed) length of about 5 mm. The fluid pump may be in a first state (for instance, infusing a fluid into a patient) when the spring is at the compressed length and in a second state (for instance, pulling fluid from a main reservoir to a pump chamber) when the spring is in the extended state. The inductance of the 5 mm spring may be about 160 nH (65 nH unamplified) and the inductance of the 2 mm spring may be about 220 nH (about 95 nH unamplified). Accordingly, a state of the fluid delivery pump (for instance, a patient infusion state or a chamber filling state) may be ascertained based on the inductance of the spring. In this manner, wearable fluid delivery device control components may use the status information to monitor device operations and/or perform functions based on the status information. The status information may be used to control operational aspects of a wearable fluid delivery device and/or fluid pump, such as changing fluid paths, activating pump elements, sending messages or other signals to a control device, error handling, and/or the like.

Although a compression spring or spring-based element is used in some examples in the present disclosure, embodiments are not so limited. For example, any resilient, flexible, or other element having different electrical characteristics in different configurations are contemplated in the present disclosure. Embodiments are not limited in this context.

The electrical characteristic of the spring-based element used for sensing processes is not limited to inductance as various other properties, including, without limitation, impedance, voltage, amperage, and/or the like may be used. In general, any electrical characteristic that may produce a change based on a configuration of the spring-based element is contemplated in the present disclosure.

Applications of spring-based sensors are not limited to wearable fluid delivery devices nor fluid delivery pumps, as these are provided for illustrative purposes in the present disclosure. More specifically, spring-based sensors may be used in any type of application that may involve a spring or spring-based element having different electrical characteristics based on a configuration or state of the spring.

Other embodiments are contemplated in the present disclosure.

FIG. 1 illustrates an example of an operating environment 100 that may be representative of some embodiments. As shown in FIG. 1, operating environment 100 may include a sensor system 105 for sensing status information of a mechanical device. In general, sensor system 105 may be installed, embedded, connected to, operably coupled to, or otherwise integrated within a system to determine a status of the system and/or components thereof. For example, sensor system 105 may be a part of a fluid pump system of a wearable fluid delivery device to provide status information for the fluid pump.

In some embodiments, sensor system 105 may include at least one spring 130*a-n*. In various embodiments spring 130*a-n* may be coupled to or otherwise associated with a mechanical device, such as a piston of a fluid pump (not shown, see FIG. 4). For example, spring 130*a-n* may compress and expand with each stroke cycle of the piston. Spring 130*a-n* may be formed of various materials, such as a metal, a magnetic material, a dielectric material, steel, copper, aluminum, alloys thereof, combinations thereof, and/or the like. Spring 130*a-n* may include a compression spring formed of a plurality of windings of the spring material. In some embodiments, sensor system 105 may have one spring 130*a-n*. In various embodiments, sensor system 105 may have two springs 130*a-n*. In exemplary embodiments, sensor system 105 may have from one spring to ten springs 130a-n or any value or range between these two values (including endpoints).

In some embodiments, spring 130a-n may have a compressed length and an extended length and a compression/extension difference equal to (extended length)–(compressed length). In some embodiments, spring 130a-n may have a compressed length of about 2 mm and an extended length of about 3 mm (for example, about 3.3 mm). In various embodiments, spring 130a-n may have a compressed length of about 1 mm, about 2 mm, about 3 mm, about 4 mm, about 5 mm, about 6 mm, about 7 mm, about 8 mm, about 9 mm, about 10 mm, about 15 mm, about 20 mm, about 25 mm, about 50 mm, about 100 mm, about 500 mm, about 1 cm, about 5 cm, about 10 cm, about 20 cm, and any value or range between any two of these values (including endpoints). In various embodiments, spring 130a-n may have an extended length of about 1 mm, about 2 mm, about 3 mm, about 4 mm, about 5 mm, about 6 mm, about 7 mm, about 8 mm, about 9 mm, about 10 mm, about 15 mm, about 20 mm, about 25 mm, about 50 mm, about 100 mm, about 500 mm, about 1 cm, about 5 cm, about 10 cm, about 20 cm, and any value or range between any two of these values (including endpoints). Embodiments are not limited in this context as the compressed and/or extended length of spring may be any length capable of operating according to the embodiments described in the present disclosure.

In various embodiments, spring 130a-n may have a measurable inductance of about 65 nH in the extended state and an inductance of about 96 nH in the compressed state. In some embodiments, spring 130a-n may be associated with an amplifier 132a-n configured to amplify the electrical characteristic of spring 130a-n being used by sensor system 105. In various embodiments, amplifier 132a-n may be or may include a magnetic material associated with spring 130a-n to amplify the inductance of spring 130a-n in the compressed and extended states. For example, amplifier 132a-n may cause spring 130a-n to have a measurable inductance of about 100 to about 170 nH in the extended state and an inductance of about 150 to about 220 nH in the compressed state. In some embodiments, amplifier 132a-n may amplify the inductance of spring 130a-n by about 10%, about 20%, about 30%, about 40%, about 50%, about 60%, about 70%, about 80%, about 90%, about 100%, about 200%, about 500%, and any value or range between any two of these values (including endpoints). In various embodiments, amplifier 132a-n may amplify the inductance of spring 130a-n by a factor of about 1.5, about 2, about 2.5, about 3, about 4, about 5, and any value or range between any two of these values (including endpoints).

A sensing circuitry 120 may be operably coupled to spring 130a-n. In some embodiments, sensing circuitry 120 may operate to receive electrical information or signals from spring 130a-n. In various embodiments, spring 130a-n may include two springs and sensing circuitry 120 may only be coupled to one spring (see, for example, FIG. 8). In other embodiments, spring 130a-n may include two springs and sensing circuitry 120 may be coupled to both springs (see, for example, FIG. 9). In some embodiments, using two (or more) springs 130a-n with sensing circuitry 120 may increase the detectable electrical information, for instance, inductance, of springs 130a-n sensed by sensing circuitry 120.

Sensing circuitry 120 may be configured to sense at least one electrical characteristic of spring 130a-n. For example, sensing circuitry 120 may include a circuit operative to measure an inductance of spring 130a-n. In some embodiments, sensing circuitry 120 may include an electronic oscillator, an inductor-capacitor (LC) oscillator, a Hartley oscillator, a Clapp oscillator, a Colpitts oscillator, combinations thereof, and/or the like. In various embodiments sensing circuitry 120 may be or may include a Colpitts oscillator (including variations on a standard Colpitts oscillator).

In various embodiments, sensor system 105 may include a logic device 110 configured to receive sensor information 112 from sensor circuitry 120. For example, in some embodiments, sensor information 112 may include inductance values of spring 130a-n measured by sensing circuitry 120 (for example, amplified by amplifier 132a-n). In exemplary embodiments, logic device 110 may operate to process sensor information 112 to generate status information 114. For example, sensor information 112 may include electrical characteristics of spring 130a-n (such as a signal indicating an inductance of spring 130a-n) and status information 114 may be a status ascertained based on the sensor information 112. For example, in a fluid delivery pump implementation, sensor information 112 may indicate that spring 130a-n has an inductance of about 150 nH. Logic device 110 may determine that an inductance of about 150 nH indicates that spring 130a-n is compressed and that the piston of the fluid delivery pump is extended, infusing a fluid into a patient of a wearable fluid delivery device.

Logic device 110 may include hardware, software, and/or a combination thereof that may include discrete, specialized logic and/or components, an application-specific integrated circuit, a microcontroller or processor that executes software instructions, firmware, programming instructions or programming code. For example, logic device 110 may include an MCU operative to determine status information 114 (for instance, device status) based on sensor information 112 (for instance, raw or processed raw electrical measurements of spring 130a-n).

In some embodiments, status information 114 may include predetermined or expected values. For example, for a fluid delivery pump (see, for example, FIG. 7), a set of expected inductance values for spring 130 during various stages of operation may be determined and stored in logic device 110 (for instance, in a memory device (not shown)) in a table, database, or other structure.

In one example, an expected inductance value of 200 nH may be specified when the piston is fully extended (and a corresponding spring is at full compression for the pump cycle) and an expected inductance value 100 nH may be specified when the piston is fully retracted (and the corresponding spring is at full extension for the pump cycle). Logic device 110 may determine an inductance during operation of the pump, look up the inductance in the expected inductance values, and determine a state of the pump (and/or piston). In some embodiments, the expected inductance values may include an expected inductance range and/or an expected inductance sequence. In some embodiments, if the determined inductance value during operation of the pump is out of range and/or deviates from an expected inductance sequence, logic device 110 may determine that there is an operating error with the pump. Logic device 110 or another control element may manage the operating error.

In another example, logic device 110 may receive or otherwise obtain information indicating an operating state of the pump, for instance, that the piston should be in the fully extended state. Logic device 110 may compare the expected inductance of spring 130 to determine if it matches the expected value or range. If the determined inductance does not correspond to the expected value or range, then logic device 110 may determine that there is an operating error with the fluid delivery pump. For instance, if logic device 110 determines that the piston of the fluid delivery pump is in full extension, then the expected inductance value of the corresponding spring should be the inductance when the spring is in full compression (for instance, 200 nH). If logic device 110 determines status information that the inductance of spring is not 200 nH (within a threshold variance amount), then logic device 110 may determine that there is an operating error with the fluid delivery pump (e.g., an occlusion). Logic device 110 or another control element may manage the operating error.

Figure 2:
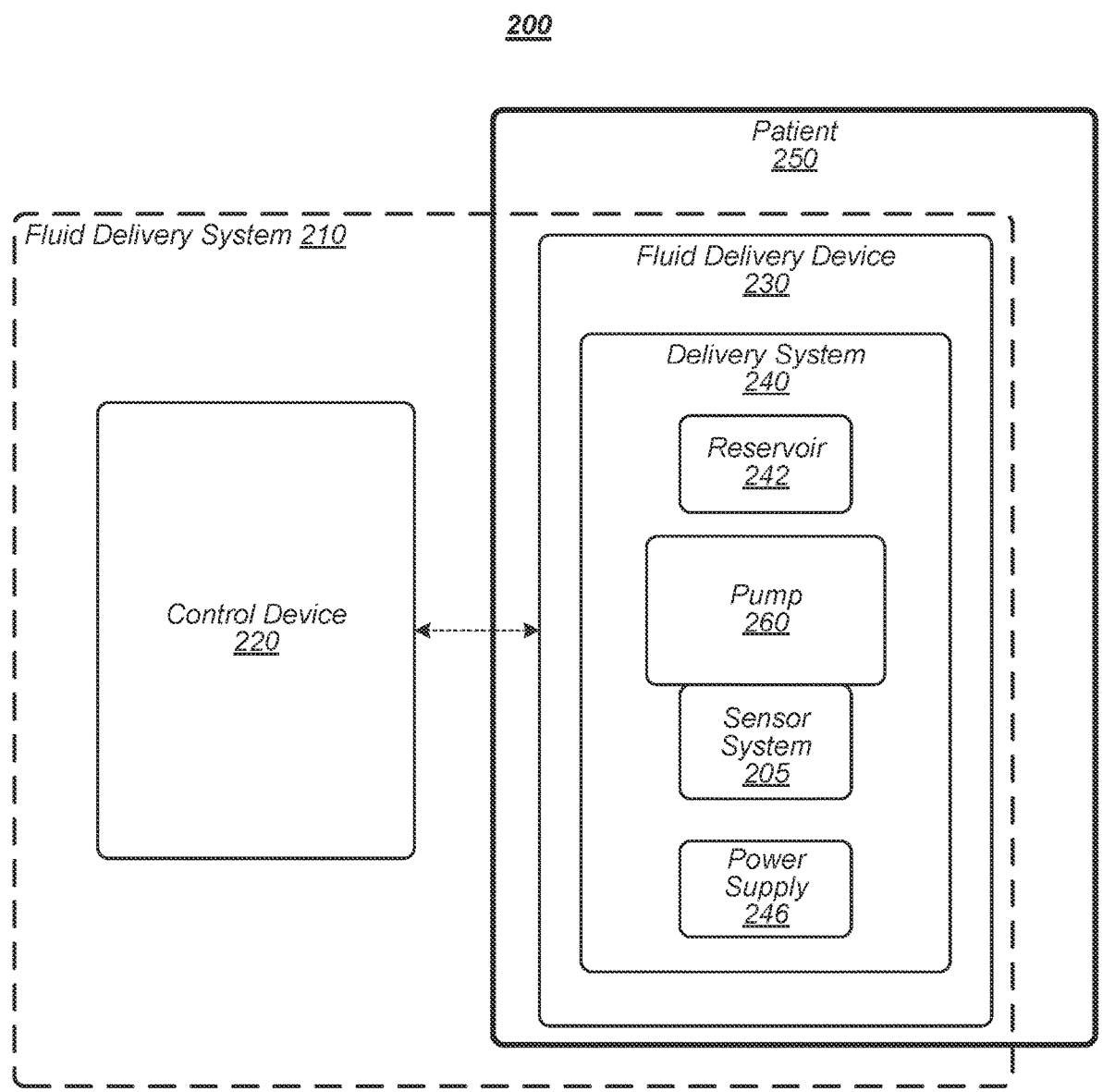
FIG. 2 illustrates a second exemplary embodiment of an operating environment in accordance with the present disclosure.

FIG. 2 illustrates an example of an operating environment 200 that may be representative of some embodiments. As shown in FIG. 2, operating environment 200 may include a fluid delivery system 210. In various embodiments, fluid delivery system 210 may include a control or computing device 220 that, in some embodiments, may be communicatively coupled to a fluid delivery device 230. Computing device 220 may be or may include one or more logic devices, including, without limitation, a server computer, a client computing device, a personal computer (PC), a workstation, a laptop, a notebook computer, a smart phone, a tablet computing device, a personal diabetes management (PDM) device, and/or the like. In some embodiments, control device 220 may be an internal control device integrated into delivery system 230, for example, as a controller, MCU, logic device, software, firmware, and/or the like. Embodiments are not limited in this context.

Fluid delivery device 230 may be or may include a wearable automatic fluid delivery device directly coupled to patient 250, for example, directly attached to the skin of the user via an adhesive and/or other attachment component. In other embodiments, fluid delivery device 230 may be coupled to patient 250 via tubing.

In some embodiments, fluid delivery device 230 may be or may include a medicament delivery device configured to deliver a liquid medicament, drug, therapeutic agent, or other medical fluid to a patient. Non-limiting examples of medicaments may include insulin, glucagon, pain relief drugs, hormones, blood pressure medicines, morphine, methadone, chemotherapy drugs, proteins, antibodies, and/or the like.

In some embodiments, fluid delivery device 230 may be or may include an automatic insulin delivery (AID) device configured to deliver insulin (and/or other medication) to patient 250. For example, fluid delivery device 230 may be or may include a device the same or similar to an OmniPod® device or system provided by Insulet Corporation of Acton, Massachusetts, United States, for example, as described in U.S. Pat. Nos. 7,303,549; 7,137,964; and/or 6,740,059, each of which is incorporated herein by reference in its entirety. Although an AID device and insulin are used in examples in the present disclosure, embodiments are not so limited, as fluid delivery device 230 may be or may include a device capable of storing and delivering any fluid therapeutic agent, drug, medicine, hormone, protein, antibody, and/or the like.

Fluid delivery device 230 may include a delivery system 240 having a number of components to facilitate automated delivery of a fluid to patient 250, including, without limitation, a reservoir 242 for storing the fluid, a pump 260 for transferring the fluid from reservoir 242, through a fluid path or conduit, and into the body of patient 250, and/or a power supply 246. Fluid delivery device 230 may include at least one penetration element (not shown) configured to be inserted into the skin of the patient to operate as a conduit between reservoir 242 and patient 250. For example, penetration element may include a cannula and/or a needle. Embodiments are not limited in this context, for example, as delivery system 240 may include more or less components.

In some embodiments, computing device 220 may be a smart phone, PDM, or other mobile computing form factor in wired or wireless communication with fluid delivery device 230. For example, computing device 220 and fluid delivery device 230 may communicate via various wireless protocols, including, without limitation, Wi-Fi (i.e., IEEE 802.11), radio frequency (RF), Bluetooth™, Zigbee™, near field communication (NFC), Medical Implantable Communications Service (MICS), and/or the like. In another example, computing device 220 and fluid delivery device 230 may communicate via various wired protocols, including, without limitation, universal serial bus (USB), Lightning, serial, and/or the like. Although computing device 220 (and components thereof) and fluid delivery device 230 are depicted as separate devices, embodiments are not so limited. For example, in some embodiments, computing device 220 and fluid delivery device 230 may be a single device. In another example, some or all of the components of computing device 220 may be included in fluid delivery device 230. For example, fluid delivery device 230 may include processor circuitry, logic circuitry, sensor circuitry, MCU, memory unit, and/or the like. In some embodiments, each of computing device 220 and fluid delivery device 230 may include a separate processor circuitry, memory unit, and/or the like capable of facilitating insulin infusion processes according to some embodiments, either individually or in operative combination. Embodiments are not limited in this context.

In various embodiments, pump 260 may be associated with sensor system 205 configured to determine a status of pump based on electrical information of a spring element of pump 260. In some embodiments, control device 220 may operate as a logic device (for instance, logic device 110 of FIG. 1) for sensor system 205. In exemplary embodiments, control device 220 may control operational aspects of fluid delivery device 230, delivery system 240, and/or pump 260 based on information determined by sensor system 205.

Figure 3:
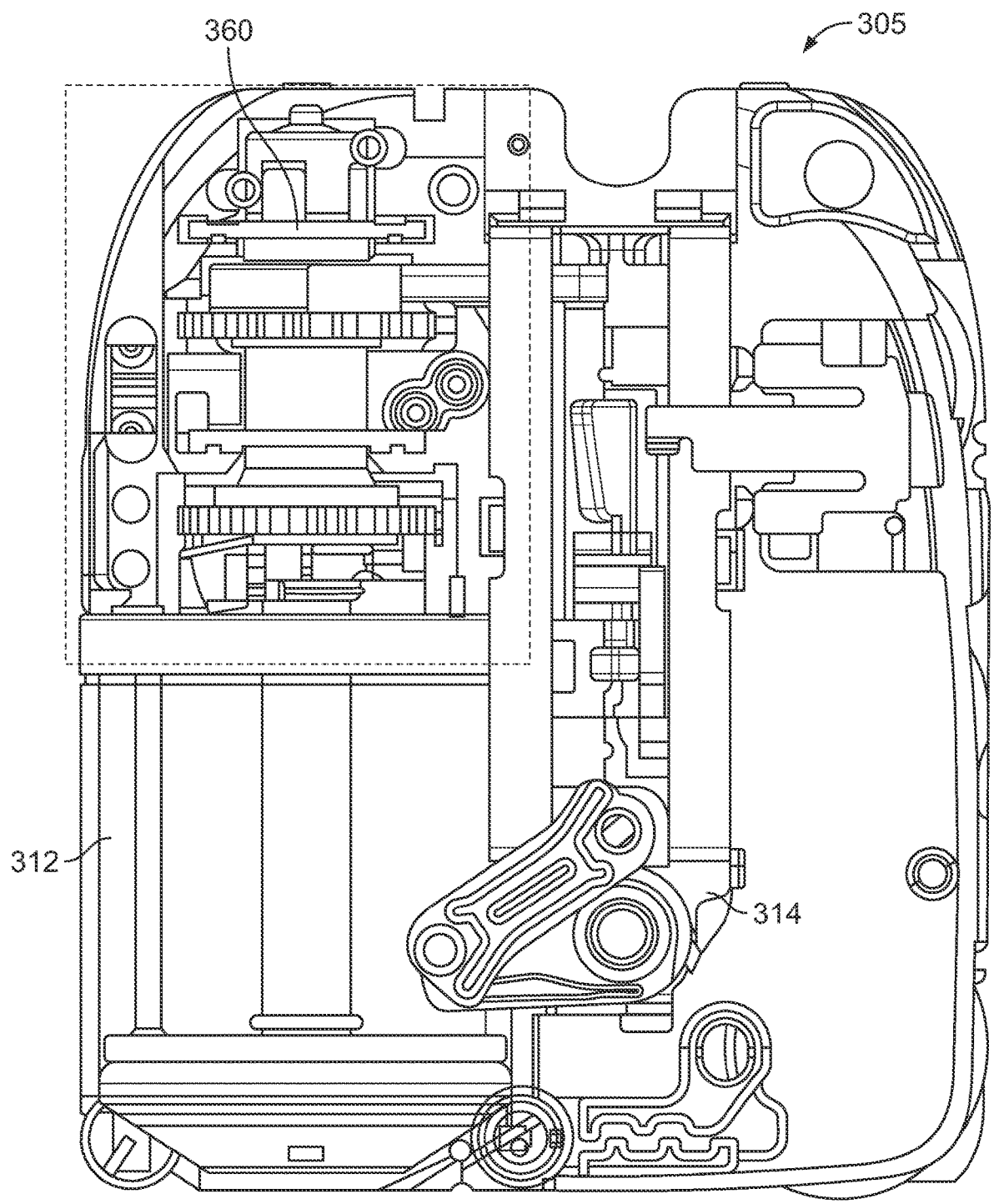
FIG. 3 illustrates an embodiment of a wearable fluid delivery device in accordance with the present disclosure.

FIG. 3 illustrates an exemplary wearable fluid delivery device in accordance with the present disclosure. In particular, FIG. 3 depicts a top-down view of a wearable fluid delivery device 305. As shown in FIG. 3, a wearable fluid delivery device 305 may include multiple systems to store and delivery a fluid to a patient. In some embodiments, wearable fluid delivery device 305 may include a pump 360. In various embodiments, pump 360 may be or may include a shuttle pump (see, for example, FIG. 4). In exemplary embodiments, wearable fluid delivery device 305 may include a reservoir 312 for storing a fluid. Reservoir may be in fluid communication with pump 360 for delivering the fluid to a patient via needle 314.

In various embodiments, pump 360 may be a linear volume shuttle pump. In some embodiments, pump 360 may be configured to deliver about 0.5 microliters per pulse. In exemplary embodiments, pump 360 may have a footprint of about 6 millimeters (mm) wide, about 11 mm long, and about 6 mm high.

Figure 4:
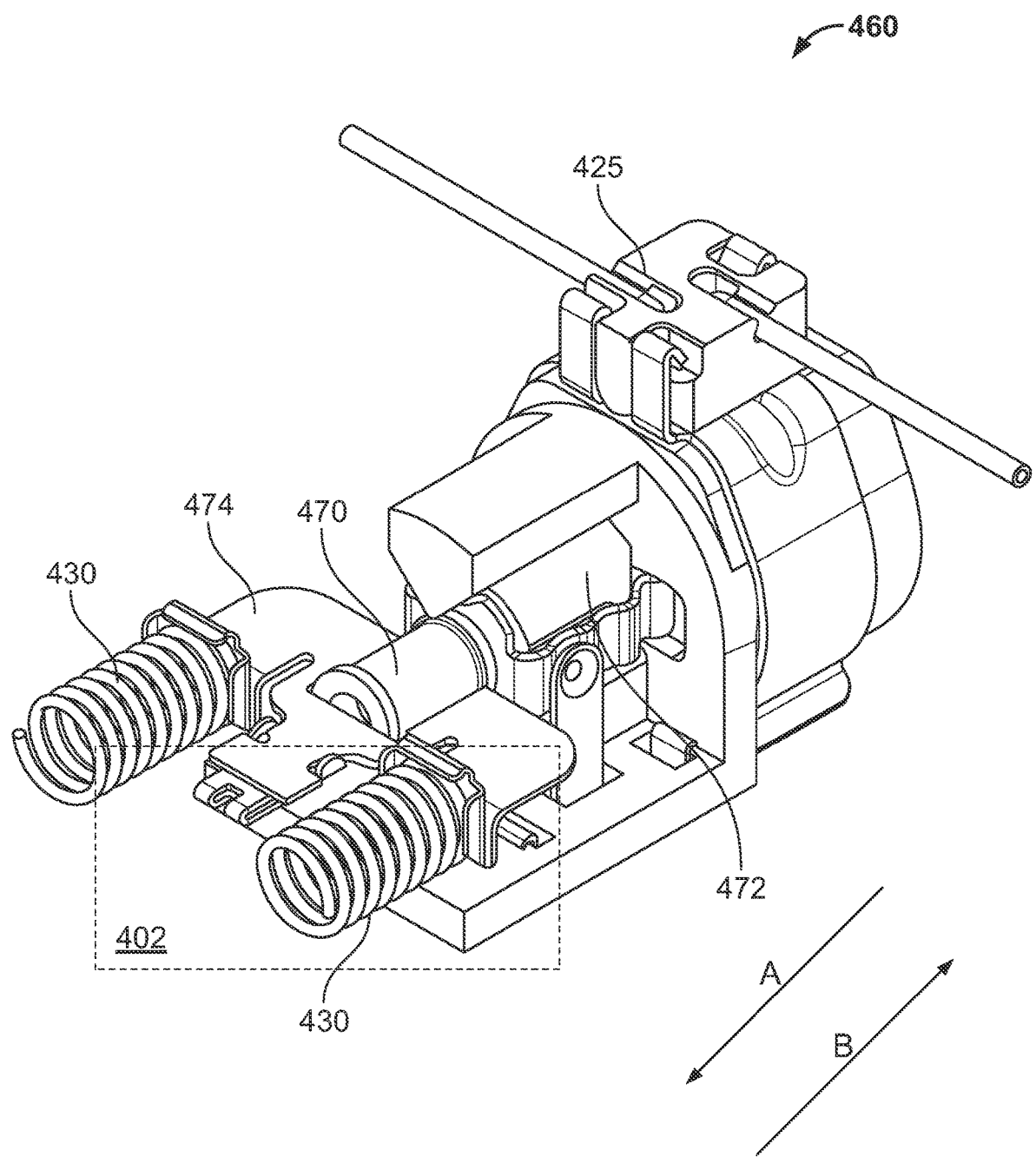
FIG. 4 illustrates an embodiment of a fluid delivery pump in accordance with the present disclosure.

FIG. 4 illustrates an embodiment of a fluid delivery pump in accordance with the present disclosure. As shown in FIG. 4, a fluid delivery pump 460 may include springs 430 attached to a carrier 474. Movement of piston 470 may move carrier 474 in one of direction A or B, causing springs 430 to compress or extend. For example, during a pump cycle, an actuator (not shown) may pull piston 470 in direction A to draw fluid into the pump chamber 472. Movement of piston 470 causes carrier 474 to also move in direction A, compressing springs 430 against a surface (not shown; see FIG. 7). Deactivation of the actuator may cause springs to extend and push on carrier 474 in direction B, thereby causing piston to move in direction B, thereby expelling the fluid in chamber 472 through port 425.

Although coil or compression springs are used in examples in the present disclosure, embodiments are not so limited. Any type of spring, coil, or other component that has detectable different electrical properties based on a configuration of the component may be used according to some embodiments. For instance, any component that may have a different inductance in one configuration than in a different configuration may be used according to some embodiments. Non-limiting examples of components may include wave springs, torsional springs, coils, (flexible) wires, and/or the like.

Figure 5A:
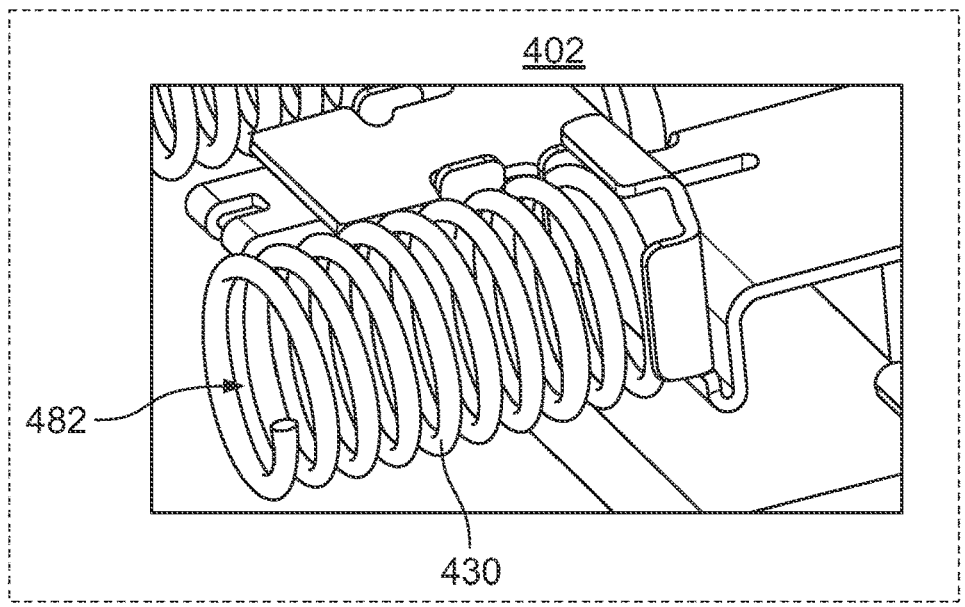
FIGS. 5A and 5B illustrate embodiments of a spring element in accordance with the present disclosure.
Figure 5B:
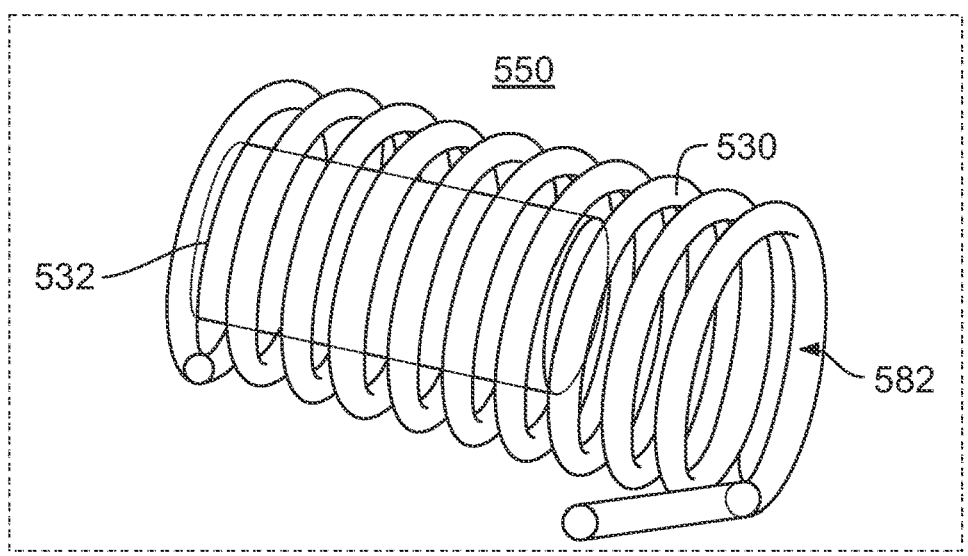
Figure 5B:
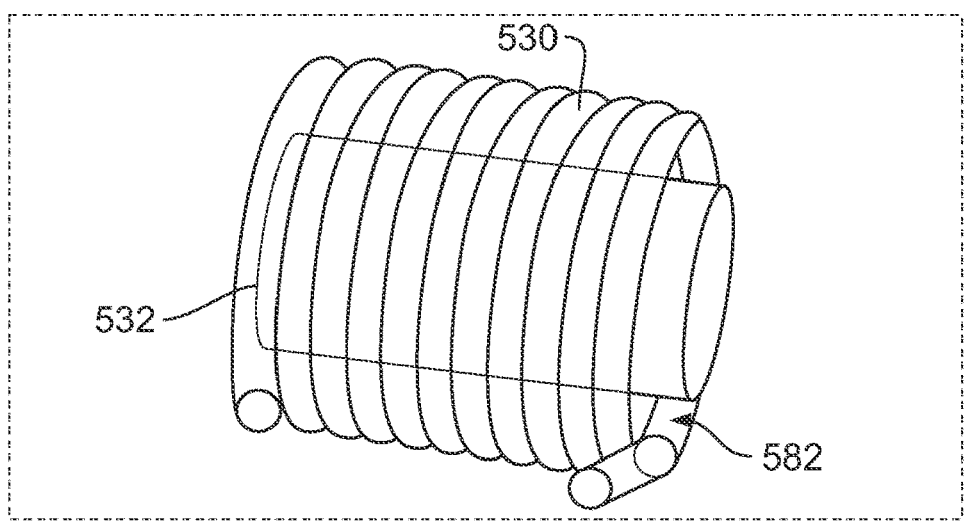

FIGS. 5A and 5B illustrate embodiments of a spring element in accordance with the present disclosure. Referring to FIG. 5A, therein is depicted spring 430 in area 402 of FIG. 4. As shown in FIG. 5A, spring 430 may have an internal space 482. As shown in FIG. 5B, an amplifier 532 may be arranged within an internal space 582 of a spring 530. In some embodiments, amplifier 532 may be or may include a magnet, magnetic material, iron, nickel, cobalt, steel, ferrite material (for instance, a ferrite material having a relative magnetic permeability of about 2000 μ/μ0), ferromagnetic materials, paramagnetic materials, diamagnetic materials, electromagnets, combinations thereof, and/or the like. In state 550, spring 530 is in an extended state and in state 551, spring 530 is in a compressed state.

In some embodiments, amplifier 532 may operate to boost, enhance, or otherwise amplify the inductance of spring 530 via inserting magnetic materials into internal space 582 of spring 532, without being bound by theory, may operate the same or similar to a solenoid from a magnetostatics perspective. In various embodiments, amplifier 532 may have a cylindrical or substantially cylindrical shape. However, amplifier 532 may have various other shapes, including cubed, cuboidal, prismatic, round or rounded, rectangular, and/or the like. In some embodiments, an axis of amplifier (for instance, in the form of a magnetic cylinder) may be aligned with an axis of the solenoid formed by spring 530. Without being bound by theory, the inserted magnetic materials may increase the inductance of a solenoid (for instance, spring 530), thereby amplifying the inductance electrical characteristic of spring 530. As spring 530 is compressed, more coils of spring 530 surround amplifier 532, compared to when spring 530 is in a relaxed state (uncompressed and untensioned), and thus produces a different inductance electrical characteristic of spring 530. And when spring 530 is in an extended state 551, fewer coils of spring 530 surround amplifier 532, compared to when spring 530 is in a relaxed state, and thus produces a different inductance electrical characteristic of spring 530. In both cases, a difference in the inductance electrical characteristic of spring 530 can be detected and such information used according to some embodiments described in the present disclosure.

Figure 6A:
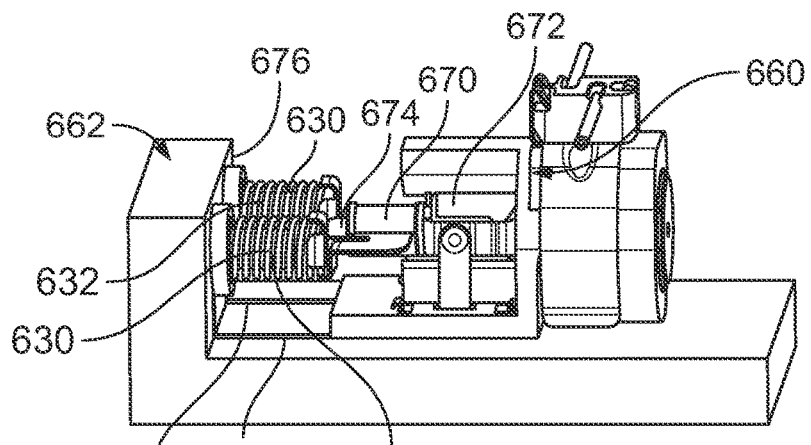
FIGS. 6A and 6B illustrate an embodiment of a fluid delivery pump in accordance with the present disclosure.
Figure 6B:
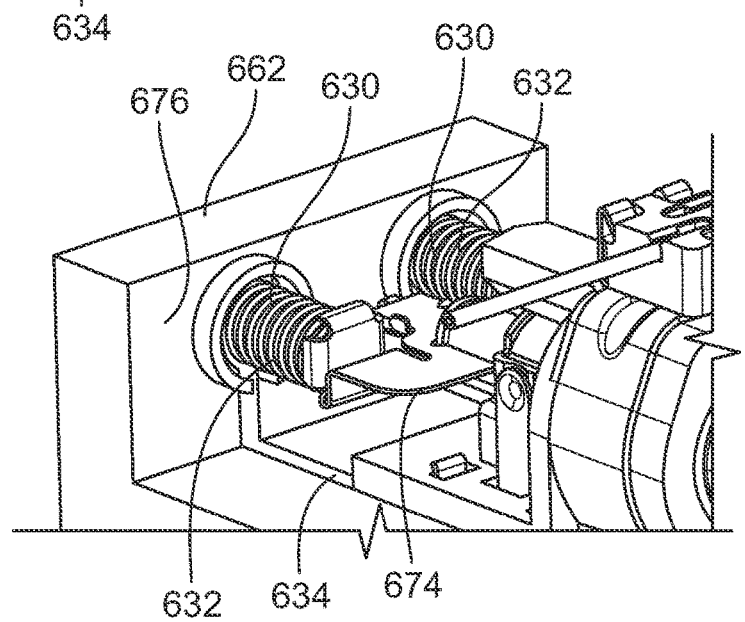

FIGS. 6A and 6B illustrate an embodiment of a fluid delivery pump in accordance with the present disclosure. As shown in FIGS. 6A and 6B, a fluid delivery pump 660 may be affixed to a chassis 662. Springs 630 may be coupled to pump 660 via carrier 674 on a first side and a surface 676 of chassis 662 on a second side. Actuation of a piston 670 may cause compression of springs 630 as piston 670 pushes springs 630 against surface 676. Springs 630 may extend as piston 670 is deactivated, moving away from surface 676.

In some embodiments, amplifiers 632 may be arranged within one or both of spring 630. In various embodiments, amplifiers 632 may be affixed to surface 676. In other embodiments, amplifiers 632 may be affixed to carrier 674. In some embodiments, amplifiers 632 may have a length such that springs 630 may compress without a portion of pump 660 (when amplifiers 632 are affixed to surface 674), surface 674 (when amplifiers 632 are affixed to carrier 674), and/or springs 630 contacting amplifiers 632. In exemplary embodiments, amplifiers 632 may be sized and positioned such that amplifiers 632 are not contacted by any portions of pump 660 or chassis 662 (except for the portion that the amplifiers 632 are affixed to). In some embodiments, amplifiers 632 may be arranged as anti-buckling supports, for example, made out of magnetic-directing material.

In various embodiments, circuitry 634 may be operably coupled to one or both of spring 632 to allow for transmission of electrical signals, such as an inductance or signals that may be used to determine inductance, to be transmitted, for example, to a sensing circuitry, logic device, and/or the like for use according to some embodiments. For example, circuitry 634 may be operably coupled to a PCB board within a wearable medical fluid device enclosing pump 660. In this manner, circuitry 634 may carry electrical signals to/from springs 630.

Figure 6C:
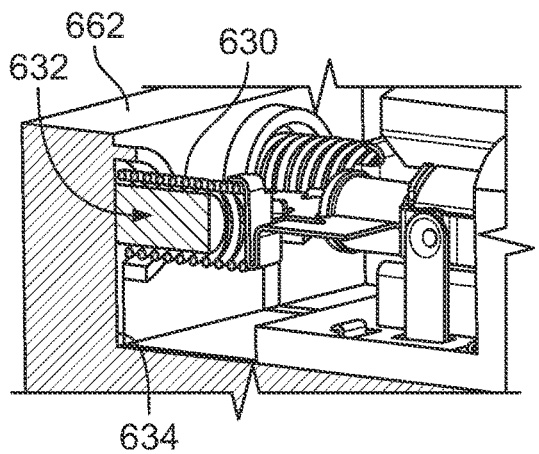
FIGS. 6C and 6D illustrates a spring element of the fluid delivery pump of FIGS. 6A and 6B.
Figure 6D:
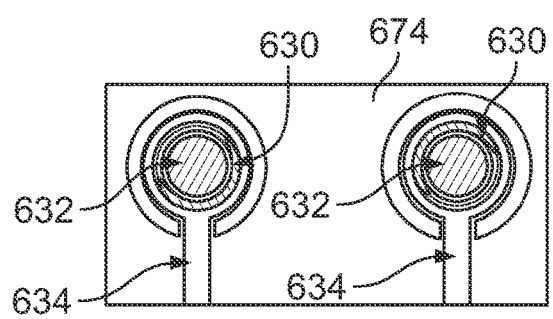

FIGS. 6C and 6D illustrates a spring element of the fluid delivery pump of FIGS. 6A and 6B. More specifically, FIG. 6C depicts a partial sectional view of pump 660 showing an internal view of spring 630 and amplifier 632. FIG. 6D depicts a front view of springs 630 depicting the arrangement of springs 630, amplifiers 632, and circuitry 634.

Figure 7:
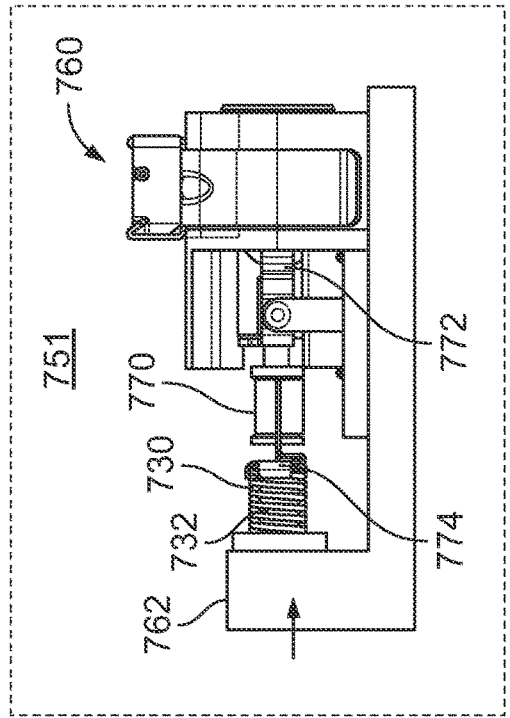
FIG. 7 illustrates exemplary operation of an embodiment of a fluid delivery pump in accordance with the present disclosure.
Figure 7:
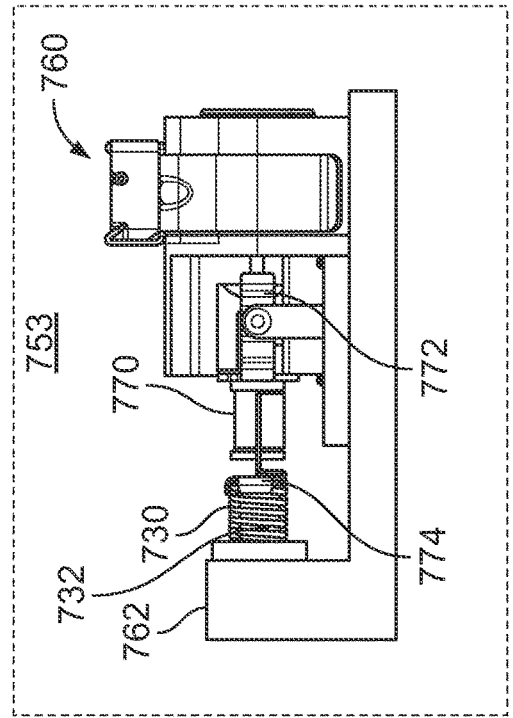
Figure 7:
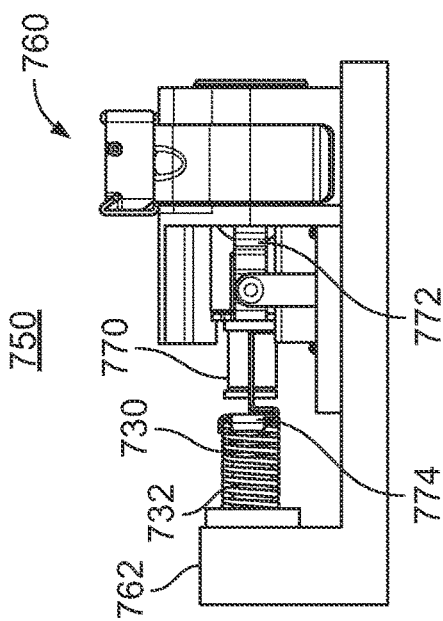
Figure 7:
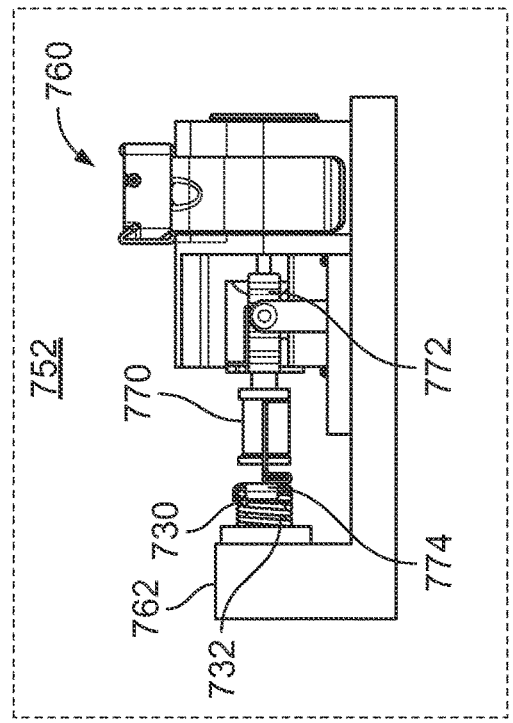

FIG. 7 illustrates exemplary operation of an embodiment of a fluid delivery pump in accordance with the present disclosure. As shown in FIG. 7, a pump 760 arranged in a chassis 762 may include a piston 770 operably coupled to a carrier 774. A spring (or springs) 730 may be coupled to carrier 774 on a first end and a surface of chassis 762 on a second end such that actuation of pump 770 toward a surface of chassis 762 may cause compression of spring 730. Movement of piston 770 away from the surface of chassis 762 may cause carrier 774 to pull spring 730 in a direction away from the surface of chassis 762 and, thereby, cause an extension of spring 730. States 750-753 of FIG. 7 depict an actuation cycle of pump 760.

State 750 depicts an initial state of pump 760. In state 751, piston 770 moves toward the surface of chassis 762, compressing spring 730 and causing a change in the inductance of spring 730 and increasing an overlap between the material of spring 730 and amplifier 732 (for instance, an increase in the number of windings of spring 730 are overlapping amplifier 732). In state 752, piston 770 and chamber 772 move toward the surface of chassis 762, leading to further compression of spring 730 and an increase in the change of inductance of spring 730 and overlap among spring 730 and amplifier. In state 753, piston 770 moves away from the surface of chassis 762 (toward chamber 772), leading to a relaxation or extension of spring that causes a change in the inductance of spring 730 and a reduction in the overlap among spring 730 and amplifier 732. After state 753, pump 760 may return to initial state 750. Accordingly, as pump 760 goes through a pump cycle, the inductance of spring 730 may be used to determine a state of pump 760 and/or components thereof, such as piston 770.

Figure 8:
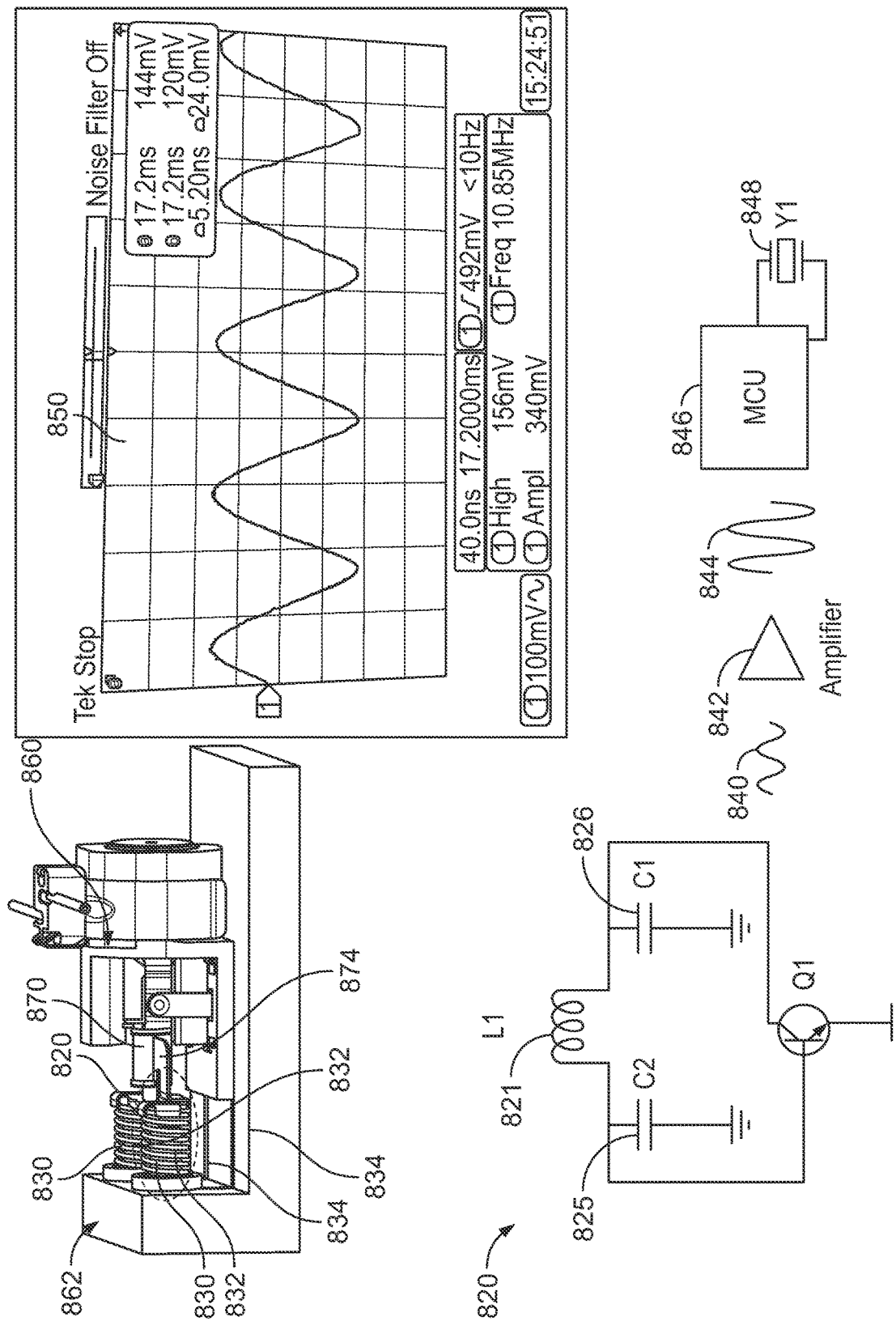
FIG. 8 illustrates a first embodiment of sensing circuitry in accordance with the present disclosure.

FIG. 8 illustrates an embodiment of a detection circuit in accordance with the present disclosure. As shown in FIG. 8, a sensing circuitry 820 may be operably coupled to a mechanical device 860 to determine an operational status of mechanical device 860. For exemplary purposes, mechanical device 860 is a fluid delivery pump arranged on a chassis 862. Fluid delivery pump 860 may include a piston 870 operably coupled to a carrier 874. Springs 830 may be coupled to carrier 874 on a first end and a surface of chassis 862 on a second end such that actuation of pump 870 toward a surface of chassis 862 may cause compression of springs 830. Movement of piston 870 away from the surface of chassis 862 may cause carrier 874 to pull spring 830 in a direction away from the surface of chassis 862 and, thereby, cause an extension of spring 830. The inductance of springs 830 may change based on the length of springs 830. In some embodiments, amplifiers 832 may be associated with springs 830 to amplify the inductance signals of springs 830.

In some embodiments, sensing circuitry 820 may be associated with one of springs 830. In various embodiments, sensing circuitry 820 may be or may include an oscillator circuit. In some embodiments, sensing circuitry 820 may be or may include a Colpitts oscillator. In various embodiments, sensing circuitry 820 and/or components thereof may be implemented on a PCB board or other substrate electrically coupled to one or both of springs 830 via circuitry 834.

In various embodiments, sensing circuitry 820 may include an oscillator in the form of a Colpitts oscillator of a common-emitter configuration. In some embodiments, Colpitts oscillator 820 may include an inductor 821 and two capacitors 825, 826. Colpitts oscillator 820 may include or may be associated with other circuitry or electrical components not depicted in FIG. 8, such as additional inductors, additional capacitors, resistors, voltage sources, amplifiers, signal processors, and/or the like. In the example embodiment depicted in FIG. 8, Colpitts oscillator 820 is a single coil oscillator associated with one spring 830.

In general, a Colpitts oscillator is tuned by the resonance between inductor 821 and the combined capacitance of capacitors 825 and 826 connected in series, operating as a tapped capacitive voltage divider (C1/C2). Single coil inductor 821 may serve as the series inductor in the PI feedback LC network. The resonant frequency depends on the inductance of spring 830 which is different when spring 830 is compressed (higher inductance) and uncompressed or extended (lower inductance). The resonance frequency may be calculated as follows:

$$f_r = \frac{1}{2\pi\sqrt{L_1 \frac{C_1 C_2}{C_1 + C_2}}} \quad (1)$$

Colpitts oscillator 820 may output a signal 840. In some embodiments, signal 840 may be provided to an amplifier 842 to generate an amplified signal 844. Signal 840 (or amplified signal 844) may be provided to a logic device, such as an MCU 846 to determine the oscillation of Colpitts oscillator 820. In one example, a timer module of MCU 846 may count the oscillation (timer incremental) during a period of time set by a reference clock Y1 848. The number of count and the duration of counting could be used to calculate the frequency. In another example, MCU 846 may include an analog-to-digital converter (ADC) to continuously sample the oscillating wave. A time-domain to frequency-domain conversion (for instance, a Fast Fourier Transformation) may be used to calculate the oscillating frequency. The oscillating frequency may be used to determine the inductance of spring 830 using processes known to those of skill in the art, for example:

$$X_L = 2\pi \times f \times L, \quad (2)$$

where $X_L$, is inductive reactance measured in ohms, 2 is a constant (2×3.1416=6.28), f is the AC frequency of the electrical supply in Hertz, and L is the inductance value of the coil in Henries. In general, without being bound by theory, when measuring the resonant frequency, inductance (L) is the variable, and the capacitance is constant. In an example, signal 840 (or signal 844) may be analyzed or displayed, for instance, on display 850 during operation of pump 860.

Figure 9:
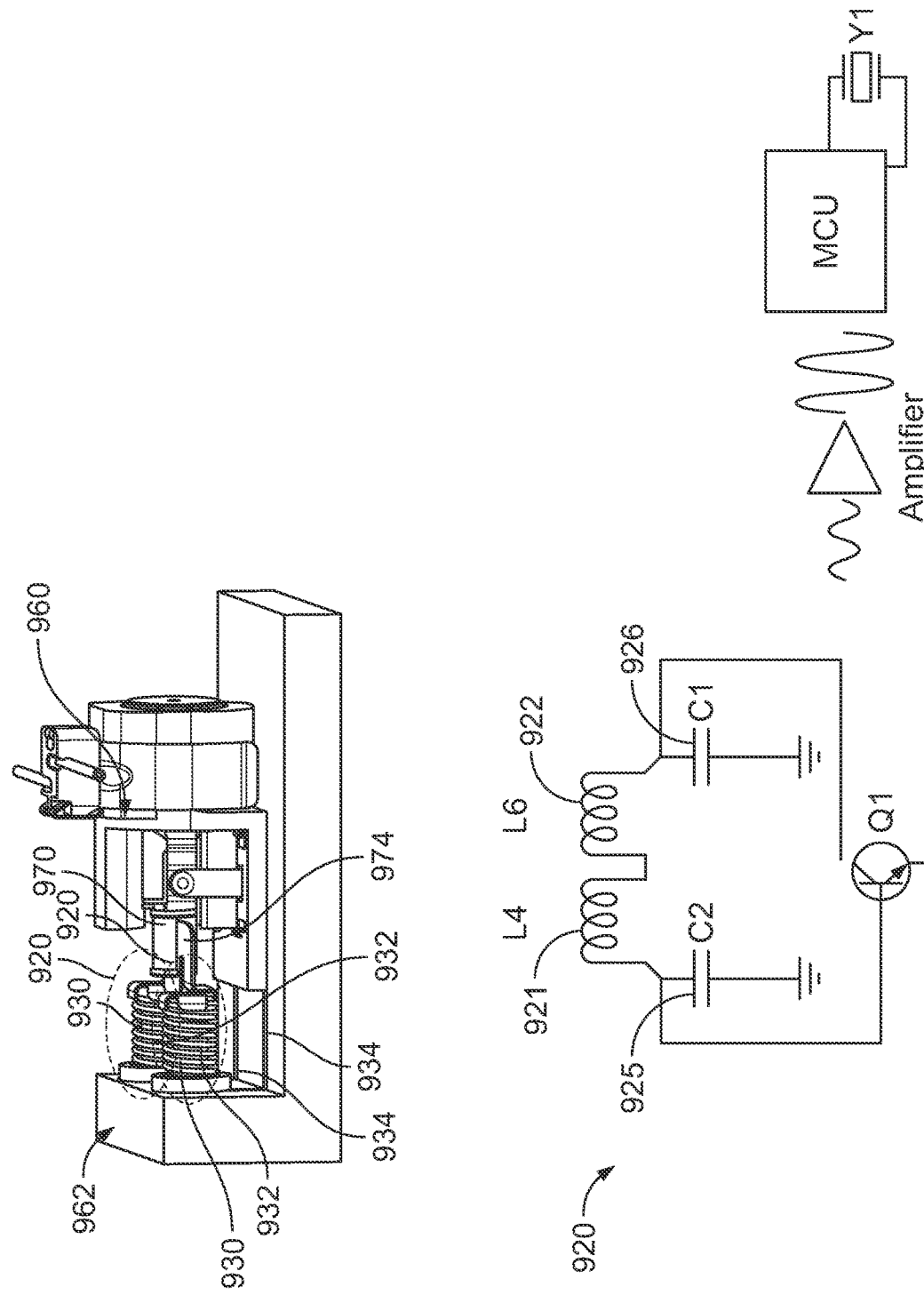
FIG. 9 illustrates a second embodiment of sensing circuitry in accordance with the present disclosure.

FIG. 9 illustrates an embodiment of a dual detection circuit in accordance with the present disclosure. As shown in FIG. 9, a sensing circuitry 920 may be operably coupled to a mechanical device 960 to determine an operational status of mechanical device 960. For exemplary purposes, mechanical device 960 is a fluid delivery pump arranged on a chassis 962 and has a piston 970 operably coupled to a carrier 974. Springs 930 may be coupled to carrier 974 on a first end and a surface of chassis 962 on a second end. In some embodiments, amplifiers 932 may be associated with springs 930 to amplify the inductance signals of springs 930.

In some embodiments, sensing circuitry 920 may be or may include a Colpitts oscillator in the form of a serialized two-spring oscillator, for example, a single spring oscillator with two springs connected in series. Colpitts oscillator 920 may include capacitors 925 and 926 and inductors 921 (L4) and 922 (L6) connected in series. Inductor 921 may be associated with one of springs 930 and inductor 922 may be associated with the other of springs 930. Accordingly, in some embodiments, two springs 930 may be used in parallel or in series to increase the range of detectable inductance.

In the serialized two-coil single oscillator configuration of Colpitts oscillator 920, the oscillation frequency may be determined using:

$$f_r = \frac{1}{2\pi\sqrt{(L_4 + L_6)\frac{C_1 C_2}{C_1 + C_2}}} \quad (3)$$

Figure 10:
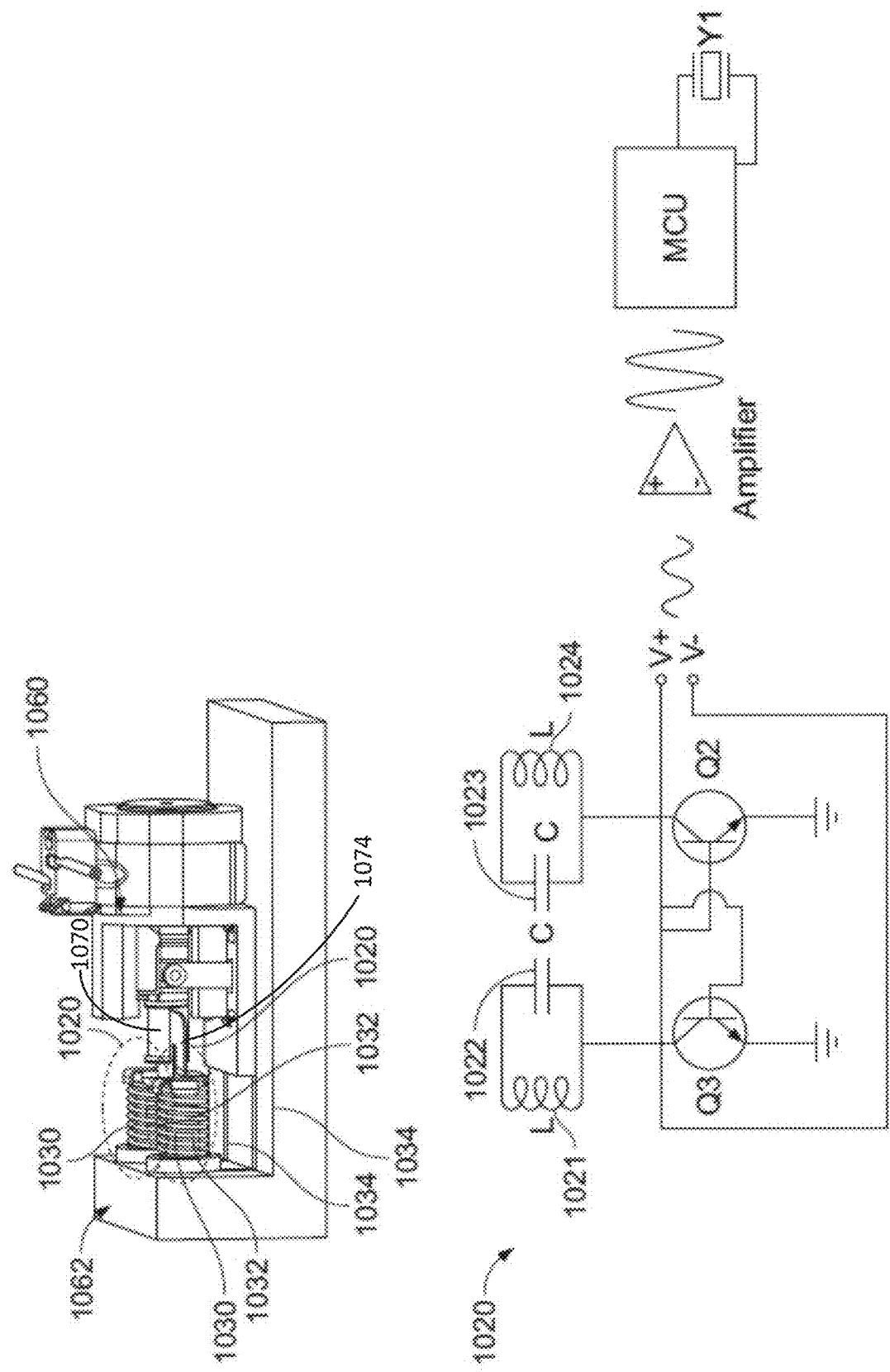
FIG. 10 illustrates a third embodiment of sensing circuitry in accordance with the present disclosure.

FIG. 10 illustrates an embodiment of a dual detection circuit according to the present disclosure. As shown in FIG. 10, a sensing circuitry 1020 may be operably coupled to a mechanical device 1060 to determine an operational status of mechanical device 1060. For exemplary purposes, mechanical device 1060 is a fluid delivery pump arranged on a chassis 1062 and has a piston 1070 operably coupled to a carrier 1074. Springs 1030 may be coupled to carrier 1074 on a first end and a surface of chassis 1062 on a second end. In some embodiments, amplifiers 1032 may be associated with springs 1030 to amplify the inductance signals of springs 1030.

In some embodiments, sensing circuitry 1020 may be or may include a Colpitts oscillator in the form of a dual-coil oscillator. Colpitts oscillator 1020 may be configured to use both of springs 1030 as part of a differential oscillator circuit. For example, Colpitts oscillator 1020 may be in the form of a cross-coupled oscillator of a common-emitter configuration in which each spring (or coil inductor) serves as part of the LC tank for oscillation. The resonant frequency depends on the inductance of springs 1020 which are different when springs 1020 are compressed (higher inductance) and uncompressed (lower inductance). The resonance frequency may be calculated as follows:

$$f_r = \frac{1}{2\pi\sqrt{LC}} \qquad (4)$$

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A spring-based sensor system, comprising:
    at least one spring associated with a mechanical element, the at least one spring operative to change from a first state to a second state based on a configuration of the mechanical element;
    sensing circuitry configured to determine an electrical property of the at least one spring, the electrical property to have a first value when the at least one spring is in the first state and a second value when the at least one spring is in the second state;
    at least one amplifier associated with the at least one spring and configured to amplify the electrical property and boost an intrinsic inductance value of the at least one spring to increase an inductance range of detection; and
    a logic device to determine a status of the mechanical element based on the electrical property.

2. A spring-based sensor system, comprising:
    at least one spring associated with a mechanical element, the at least one spring operative to change from a first state comprising a compressed state to a second state comprising an extended state based on a configuration of the mechanical element;
    sensing circuitry configured to determine an electrical property of the at least one spring, the electrical property to have a first value when the at least one spring is in the first state and a second value when the at least one spring is in the second state;
    at least one amplifier associated with the at least one spring and configured to amplify the electrical property and boost an intrinsic inductance value of the at least one spring to increase an inductance range of detection; and
    a logic device to determine a status of the mechanical element based on the electrical property.

3. The spring-based sensor system of claim 2, the electrical property comprising an inductance of the at least one spring.

4. The spring-based sensor system of claim 3, the at least one spring having a length of about 2 millimeters (mm) in the compressed state and a length of about 3 mm in the extended state.

5. The spring-based sensor system of claim 3, the at least one amplifier comprising a magnetic material arranged within an internal space of the at least one spring.

6. The spring-based sensor system of claim 3, the at least one amplifier to amplify the inductance of the at least one spring by a factor of about 2 to about 3.

7. The spring-based sensor system of claim 3, the at least one amplifier comprising a cylinder of magnetic material.

8. The spring-based sensor system of claim 7, an axis of the cylinder of the amplifier having an axis aligned with an axis of the at least one spring to form a solenoid.

9. The spring-based sensor system of claim 1, the sensing circuitry comprising an oscillator.

10. The spring-based sensor system of claim 9, the at least one spring comprising two springs, each of the two springs electrically coupled to one of two inductor-capacitor circuits of a cross-coupled oscillator circuit.

11. The spring-based sensor system of claim 1, the sensing circuitry comprising a Colpitts oscillator.

12. The spring-based sensor system of claim 11, the at least one spring comprising two springs, each of the two springs electrically coupled to one of two inductors of the Colpitts oscillator.

13. A fluid delivery device, comprising:
    a fluid delivery pump system;
    the spring-based sensor system of claim 1 operatively coupled to the fluid delivery pump system, the at least one spring operatively coupled to a piston of the fluid delivery pump system such that the at least one spring enters the first state and the second state based on a position of the piston;
    a logic device configured to determine a status of the fluid delivery pump system based on sensor information generated by the spring-based sensor system.

14. The fluid pump system of claim 13, the sensor information comprising an inductance of the at least one spring.

15. The fluid pump system of claim 14, the logic device operably coupled to a memory configured to store expected inductance values.

16. The fluid pump system of claim 15, the logic device to determine an operational status of the fluid delivery pump by comparing the sensor information with expected inductance values.

17. The fluid pump system of claim 16, the logic to generate an error responsive to the inductance of the at least one spring not corresponding to an expected inductance value.

18. The fluid pump system of claim 13, the logic device comprising a microcontroller (MCU).

19. The fluid pump system of claim 16, the logic device to determine a position of the piston based on the inductance of the at least one spring.

\* \* \* \* \*